(12) United States Patent
Mertoglu et al.

(10) Patent No.: US 10,316,131 B2
(45) Date of Patent: Jun. 11, 2019

(54) HYPERBRANCHED POLYMER MODIFIED WITH ISOCYANATE LINKER AND MIX OF SHORT AND LONG CHAIN ALKYL POLYETHER

(71) Applicant: BASF SE, Ludwigshafen (DE)

(72) Inventors: Murat Mertoglu, Sao Paolo Vila Gertrudes (BR); Felix Alexander Westerhaus, Mannheim (DE); Daniel Stadler, Shanghai (CN); Benedikt Crone, Mannheim (DE); Ann-Kathrin Marguerre, Mannheim (DE); Rainer Berghaus, Speyer (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/540,187

(22) PCT Filed: Dec. 11, 2015

(86) PCT No.: PCT/EP2015/079344
§ 371 (c)(1),
(2) Date: Jun. 27, 2017

(87) PCT Pub. No.: WO2016/102203
PCT Pub. Date: Jun. 30, 2016

(65) Prior Publication Data
US 2017/0327621 A1    Nov. 16, 2017

(30) Foreign Application Priority Data

Dec. 23, 2014 (EP) .................................... 14200167
Sep. 7, 2015 (EP) .................................... 15184093

(51) Int. Cl.
| | | |
|---|---|---|
| A01N 25/04 | (2006.01) |
| A01N 43/653 | (2006.01) |
| A01N 43/56 | (2006.01) |
| A01N 47/02 | (2006.01) |
| A61K 31/216 | (2006.01) |
| A61K 31/55 | (2006.01) |
| A61K 47/34 | (2017.01) |
| C08G 18/40 | (2006.01) |
| C08G 18/42 | (2006.01) |
| C08G 18/44 | (2006.01) |
| C08G 18/48 | (2006.01) |
| C08G 18/60 | (2006.01) |
| C08G 18/64 | (2006.01) |
| C08G 18/75 | (2006.01) |
| C08G 83/00 | (2006.01) |
| A01N 25/30 | (2006.01) |

(Continued)

(52) U.S. Cl.
CPC ............. *C08G 18/44* (2013.01); *A01N 25/04* (2013.01); *A01N 25/30* (2013.01); *A01N 43/56* (2013.01); *A01N 43/653* (2013.01); *A01N 47/02* (2013.01); *A61K 31/216* (2013.01); *A61K 31/55* (2013.01); *A61K 47/34* (2013.01); *C08G 18/222* (2013.01); *C08G 18/282* (2013.01); *C08G 18/283* (2013.01); *C08G 18/346* (2013.01); *C08G 18/4018* (2013.01); *C08G 18/4081* (2013.01); *C08G 18/4236* (2013.01); *C08G 18/4238* (2013.01); *C08G 18/4247* (2013.01); *C08G 18/4252* (2013.01); *C08G 18/4263* (2013.01); *C08G 18/4804* (2013.01); *C08G 18/4854* (2013.01); *C08G 18/5024* (2013.01); *C08G 18/603* (2013.01); *C08G 18/6415* (2013.01); *C08G 18/6438* (2013.01); *C08G 18/755* (2013.01); *C08G 18/7671* (2013.01); *C08G 18/792* (2013.01); *C08G 65/33355* (2013.01); *C08G 69/40* (2013.01); *C08G 69/44* (2013.01); *C08G 83/005* (2013.01); *C08G 83/006* (2013.01); *C08L 71/02* (2013.01); *C08G 2650/32* (2013.01)

(58) Field of Classification Search
None
See application file for complete search history.

(56) References Cited

U.S. PATENT DOCUMENTS

| 6,399,048 B1 | 6/2002 | Allard et al. |
| 2012/0053221 A1 | 3/2012 | Ishaque et al. |

(Continued)

FOREIGN PATENT DOCUMENTS

| DE | 4319671 A1 | 12/1994 |
| DE | 4319672 A1 | 12/1994 |

(Continued)

OTHER PUBLICATIONS

Extended European Search Report for EP Application No. 14200167.6, dated May 13, 2015, 8 pages.

(Continued)

*Primary Examiner* — Alicia L Otton
(74) *Attorney, Agent, or Firm* — Armstrong Teasdale LLP

(57) ABSTRACT

The invention relates to a hyperbranched polymer comprising:
a) a hyperbranched polycondensate with hydroxyl end groups, amino end groups, or a combination thereof condensed to
b) one or more linking groups connected to
c1) one or more polyethylene glycol monomethyl ethers and
c2) one or more poly($C_2$-$C_3$)alkylene glycol mono-($C_8$-$C_{22}$)-alkyl ethers, wherein the weight ratio of components c1):c2) is from 9:1 to 1:9. It further relates to a process for producing the polymer, to a composition comprising the polymer and an active ingredient, and to a method for controlling phytopathogenic fungi or undesired vegetation or insect or acarid infestations or for regulating the growth of plants.

18 Claims, No Drawings

(51) Int. Cl.
*C08G 18/28* (2006.01)
*C08L 71/02* (2006.01)
*C08G 65/333* (2006.01)
*C08G 18/50* (2006.01)
*C08G 18/76* (2006.01)
*C08G 18/79* (2006.01)
*C08G 18/22* (2006.01)
*C08G 18/34* (2006.01)
*C08G 69/40* (2006.01)
*C08G 69/44* (2006.01)

(56) References Cited

U.S. PATENT DOCUMENTS

| | | | |
|---|---|---|---|
| 2012/0054920 | A1 | 3/2012 | Tuerk et al. |
| 2012/0309626 | A1 | 12/2012 | Tuerk et al. |

FOREIGN PATENT DOCUMENTS

| | | | |
|---|---|---|---|
| DE | 19519042 | A1 | 11/1996 |
| DE | 10138216 | A1 | 2/2003 |
| DE | 10147712 | A1 | 4/2003 |
| DE | 10163163 | A1 | 7/2003 |
| DE | 10219508 | A1 | 11/2003 |
| DE | 10240817 | A1 | 3/2004 |
| WO | 199723474 | A1 | 7/1997 |
| WO | 199916810 | A1 | 4/1999 |
| WO | 200146296 | A1 | 6/2001 |
| WO | 200149817 | A2 | 7/2001 |
| WO | 2006087227 | A2 | 8/2006 |
| WO | 2007068632 | A1 | 6/2007 |
| WO | 2007125028 | A1 | 11/2007 |
| WO | 2009021986 | A1 | 2/2009 |
| WO | 2009047210 | A1 | 4/2009 |
| WO | 2010130559 | A1 | 11/2010 |
| WO | 2010130680 | A2 | 11/2010 |
| WO | 2011069895 | A1 | 6/2011 |
| WO | 2011073220 | A1 | 6/2011 |
| WO | 2011073222 | A2 | 6/2011 |
| WO | 2012028496 | A1 | 3/2012 |
| WO | 2013020820 | A1 | 2/2013 |
| WO | 2014016148 | A2 | 1/2014 |
| WO | 2014032948 | A1 | 3/2014 |

OTHER PUBLICATIONS

International Preliminary Report on Patentability issued in International Application No. PCT/EP2015/079344 dated Nov. 14, 2016, 7 pages.
International Search Report issued in International Application No. PCT/EP2015/079344 dated Feb. 12, 2016, 4 pages.
Written Opinion of the International Search Authority issued in International Application No. PCT/EP2015/079344 dated Feb. 12, 2016, 7 pages.

HYPERBRANCHED POLYMER MODIFIED WITH ISOCYANATE LINKER AND MIX OF SHORT AND LONG CHAIN ALKYL POLYETHER

CROSS-REFERENCE TO RELATED APPLICATIONS

This application is a U.S. National Phase Application of PCT/EP2015/079344, filed Dec. 11, 2015, which claims the benefit of priority to EP Application No. 14200167.6, filed Dec. 23, 2014, and EP Application No. 15184093.1, filed Sep. 7, 2015.

The invention relates to specific alkoxylated hyperbranched polymers, processes for their production and their use in compositions comprising active ingredients.

In many cases it is necessary to solubilize hydrophobic active ingredients in water without chemically modifying the relevant active ingredient. For this purpose it is possible to prepare an emulsion in which the relevant active ingredient is in the oil phase of the emulsion. However, with many active pharmaceutical ingredients and crop protection agents, especially those which are to be transported with a body fluid or in a plant's sap, an approach of this kind is not possible.

Compositions comprising an active ingredient and a hyperbranched polymer as a solubilizer are known in the art. WO 2010/130680 discloses the use of various hyperbranched polymers for increasing the soil mobility of sparingly soluble insecticides. WO 2010/130559 and WO 2011/069895 disclose hyperbranched polycarbonates for solubilizing poorly soluble active ingredients. WO 2011/073220 and WO 2011/073222 disclose hyperbranched polyesters with a hydrophobic cove for solubilizing sparingly soluble active ingredients. WO 2007/125028 discloses a process for solubilizing hydrophobic active ingredients in an aqueous medium, wherein a hyperbranched polyester which has optionally been reacted with a polyalkylene oxide unit which bears an isocyanate group is used. To prepare the polyester, a wide variety of different dicarboxylic acids are described, such as sebacic acid, and a wide variety of different trifunctional alcohols, such as glycerol, trimethylolpropane, pentaerythritol and alkoxylated derivatives thereof. The polyester can be reacted with a reaction product of diisocyanate having a capped polyalkylene glycol. WO 2009/047210 discloses hyperbranched polyesters comprising dicarboxylic acid units and trifunctional alcohols, the dicarboxylic acid units described being succinic acid units substituted by $C_3$-$C_{40}$ alkyl radicals or alkenyl radicals. A wide variety of different trifunctional alcohols are mentioned, such as glycerol, trimethylolpropane, pentaerythritol and alkoxylated derivatives thereof. WO 2007/068632 discloses hyperbranched polyesters obtainable by reacting dicarboxylic acids having polyisobutene groups and trifunctional alcohols such as glycerol, trimethylolpropane, pentaerythritol and the alkoxylated derivatives thereof. The polyester can subsequently be functionalized.

Although good results are already obtained with the known hyperbranched polymers, there is still much room for improvement, in particular with respect to the amount of active ingredient that should be solubilized.

Accordingly, it was an object of the present invention to find alternative hyperbranched polymers which are suitable for solubilizing sparingly soluble active ingredients, in particular in an aqueous medium. It was a further object to find a polymer which can solubilize maximum amounts of active ingredients, especially active agrochemical ingredients, and which should have maximum stability, especially hydrolytic stability. In addition, the polymer should itself be water-soluble or water-dispersible. Finally, it was an object of the invention to find a hyperbranched polymer which is readily preparable from commercially available chemicals and on an industrial scale.

It has now been found that these objects can be achieved with a hyperbranched polymer comprising (preferably consisting of)
a) a hyperbranched polycondensate with hydroxyl and/or amino end groups condensed to
b) one or more linkers connected to
c1) one or more polyethylene glycol monomethyl ethers and
c2) one or more poly($C_2$-$C_3$)alkylene glycol mono-($C_8$-$C_{22}$)-alkyl ethers, wherein the weight ratio of components c1):c2) is from 9:1 to 1:9.

In a further aspect of the invention there is provided a process for producing a hyperbranched polymer of the invention comprising the steps of either α-1 reacting a hyperbranched polycondensate with hydroxyl and/or amino end groups with a linker (b), and α-2 reacting the product of step α-1 with a mixture of at least one polyethylene glycol monomethyl ether (c1) and at least one poly($C_2$-$C_3$)-alkylene glycol mono-($C_8$-$C_{22}$)-alkyl ether, wherein the weight ratio of c1):c2) is from 9:1 to 1:9;

or

β-1 reacting a mixture of at least one polyethylene glycol monomethyl ether (c1) and at least one poly($C_2$-$C_3$)-alkylene glycol mono-($C_8$-$C_{22}$)-alkyl ether, wherein the weight ratio of c1):c2) is from 9:1 to 1:9 with a linker (b), and β-2 reacting the product of step β-1 with a hyperbranched polymer with hydroxyl and/or amino end groups.

In yet a further aspect of the invention there is provided the use of a hyperbranched polymer of the invention in a composition comprising an active ingredient, in particular in a pesticidal or pharmaceutical composition.

In another aspect of the invention there is provided the use of a hyperbranched polymer of the invention for increasing the water-solubility of sparingly water-soluble active ingredients in aqueous solutions.

In yet a further aspect of the invention there is provided a composition comprising the hyperbranched polymer of the invention and an active ingredient, in particular a pesticidal or pharmaceutical active ingredient.

In yet a further aspect of the invention there is provided a process for producing the composition of the invention comprising the step of contacting a hyperbranched polymer of the invention and a pesticidal or pharmaceutical active ingredient.

In yet a further aspect of the invention there is provided a method for controlling phytopathogenic fungi or undesired vegetation or insect or acarid infestations or for regulating the growth of plants, comprising the step of applying the composition of the invention, where the active ingredient is a pesticide, to the pests or undesired plants, to plants to be protected and/or to the soil where the plants to be protected or the undesired plants grow.

Advantages of the invention are that a high concentration of active ingredient can be brought into solution; that the preparation of the hyperbranched polymer is possible in a very simple manner and on an industrial scale; and that the hyperbranched polymer itself is water-soluble or water-dispersible. In addition, it is possible to provide hyperbranched polymer without anionic groups, such that there cannot be any unwanted interaction with the active ingredients or other formulation excipients in compositions comprising active ingredients. It is also possible to very finely adjust the polarity of the hyperbranched polymer. In addition, the compositions of the invention show an excellent storage stability.

Throughout the application, combinations of preferred features with other preferred features are encompassed by the invention.

The hyperbranched polymers of the invention comprises (preferably consist of) a core, which is a hyperbranched polycondensate a) with hydroxyl and/or amino end groups, and of a shell, which is a mixture of one or more polyethylene glycol monomethyl ethers (MPEG) (c1) and one or more poly($C_2$-$C_3$)alkylene glycol mono-($C_8$-$C_{22}$)-alkyl ethers (FAPAG) (c2) in a weight ratio of 1:9 to 9:1. Core and shell are connectedby a linker (b) which is condensed to the hydroxyl and/or amino groups of the polycondensate (a) and the hydroxyl end groups of the MPEG/FAPAG mixture (c1)/(c2).

Hyperbranched Polycondensates (a)

The hyperbranched polycondensate (a) is preferably selected from the group consisting of hyperbranched polycarbonates, polyesters, polyimides, polyurethanes, polyureas, polyamides, polythioureas, polyethers, polyestercarbonates, polyethercarbonates, polyetheresters, polyesteramides, polyesteramines, polyetherestercarbonates and polyetherurethanecarbonates. Such compounds and the preparation thereof are described, for example, in WO 2009/021986.

Preferred as hyperbranched polycondensates (a) are hyperbranched polycarbonates (a1), polyesters (a2), polyimides (a3), polyurethanes (a4) and polyureas (a5). More preferred are hyperbranched polycarbonates (a1), polyesters (a2) and polyimides (a3). Even more preferred are hyperbranched polycarbonates (a1) and polyesters (a2). Hyperbranched polyesters (a2) are particularly preferred.

By hyperbranched polycondensates or polymers for the purposes of this invention are meant noncrosslinked macromolecules having hydroxyl and/or amino end groups, which may be both structurally and molecularly nonuniform. On the one hand they may be synthesized starting from a central molecule in the same way as for dendrimers but, in contrast to the latter, with a nonuniform chain length of the branches. Hyperbranched polycondensates/polymers are therefore to be differentiated from dendrimers (U.S. Pat. No. 6,399,048). For the purposes of the invention, hyperbranched polycondensates/polymers do not comprise dendrimers. On the other hand, the hyperbranched polymers may also be of linear construction, with functional, branched side groups, or else, as a combination of the two extremes, may include linear and branched molecule moieties. For the definition of dendrimers and hyperbranched polymers see also P. J. Flory, J. Am. Chem. Soc. 1952, 74, 2718 and H. Frey et al., Chem. Eur. J. 2000, 6, 2499.

By "hyperbranched" in the context of the invention is meant that the degree of branching (DB), in other words the ratio of the sum of the average number of dendritic linkages plus the average number of end groups to the sum of the average number of dendritic and linear linkages plus the average number of end groups, per molecule, multiplied by 100, is 10% to 99.9%, preferably 20% to 99%, more preferably 20% to 95%. By "dendrimeric" in the context of the present invention is meant that the degree of branching is 99.9%-100%. For the definition of the degree of branching see H. Frey et al., Acta Polym. 1997, 48, 30.

It is a feature of the present invention that the polycondensates (a) of the invention are noncrosslinked. "Noncrosslinked" for the purposes of this specification means that the degree of crosslinking is less than 15% by weight, preferably less than 10% by weight, determined via the insoluble fraction of the polymer. The insoluble fraction of the polycondensate is determined by four-hour extraction with the same solvent as used for the gel permeation chromatography for determining the molecular weight distribution of the polymers, i.e., tetrahydrofuran, dimethylacetamide or hexafluoroisopropanol, according to which solvent has the better solvency for the polycondensate, in a Soxhlet apparatus and, after drying of the residue to constant weight, by weighing of the residue remaining.

Polycarbonates (a1)

In one preferred embodiment the hyperbranched polycondensate (a) is a hyperbranched polycarbonate. The hyperbranched polycarbonate is typically obtainable by a) preparing a condensation product (K) by reacting an organic carbonate (A) or a phosgene derivative with an alcohol (B1) which has at least three hydroxyl groups, and b) intermolecularly converting K to the hyperbranched polycarbonate, the quantitative ratio of the OH groups to the carbonate or phosgene groups being selected such that K has an average of either i) one carbonate or carbamoyl chloride group and more than one OH group, or ii) one OH group and more than one carbonate or carbamoyl group. The polycarbonate is preferably obtained in this way.

The condensation product (K) can be prepared using an organic carbonate (A) or a phosgene derivative. Examples of suitable phosgene derivatives are phosgene, diphosgene or triphosgene, preferably phosgene. It is preferred to use an organic carbonate (A). The hyperbranched polycarbonate preferably comprises an organic carbonate (A) in polymerized form.

The radicals R in the organic carbonates (A) of the general formula RO[(CO)O]$_n$R that are used as starting material are each independently of one another a straight-chain or branched aliphatic, aromatic/aliphatic (araliphatic) or aromatic hydrocarbon radical having 1 to 20 C atoms. The two radicals R may also be joined to one another to form a ring. The two radicals R may be the same or different; they are preferably the same. The radical in question is preferably an aliphatic hydrocarbon radical and more preferably a straight-chain or branched alkyl radical having 1 to 5 C atoms, or a substituted or unsubstituted phenyl radical. R in this case is a straight-chain or branched, preferably straight-chain (cyclo)aliphatic, aromatic/aliphatic or aromatic, preferably (cyclo)aliphatic or aromatic, more preferably aliphatic hydrocarbon radical having 1 to 20 C atoms, preferably 1 to 12, more preferably 1 to 6, and very preferably 1 to 4 carbon atoms. Examples of such radicals are methyl, ethyl, isopropyl, n-propyl, n-butyl, isobutyl, sec-butyl, tert-butyl, n-hexyl, n-heptyl, n-octyl, n-decyl, n-dodecyl, n-tetradecyl, n-hexadecyl, n-octadecyl, n-eicosyl, 2-ethylhexyl, cyclopentyl, cyclohexyl, cyclooctyl, cyclododecyl, phenyl, o- or p-tolyl or naphthyl. Methyl, ethyl, n-butyl, and phenyl are preferred. These radicals R may be the same or different; they are preferably the same. The radicals R may also be joined to one another to form a ring.

Examples of divalent radicals R of this kind are 1,2-ethylene, 1,2-propylene, and 1,3-propylene. Generally speaking, n is an integer from 1 to 5, preferably from 1 to 3, more preferably from 1 to 2. The carbonates may preferably be simple carbonates of the general formula RO(CO)OR, i.e. n in this case is 1.

Examples of suitable carbonates comprise aliphatic, aromatic/aliphatic or aromatic carbonates such as ethylene carbonate, 1,2- or 1,3-propylene carbonate, diphenyl carbonate, ditolyl carbonate, dixylyl carbonate, dinaphthyl carbonate, ethyl phenyl carbonate, dibenzyl carbonate, dimethyl carbonate, diethyl carbonate, di-n-propyl carbonate, di-n-butyl carbonate, diisobutyl carbonate, dipentyl carbonate, dihexyl carbonate, dicyclohexyl carbonate, diheptyl carbonate, dioctyl carbonate, didecyl carbonate or didodecyl carbonate. Examples of carbonates in which n is greater than 1 comprise dialkyl dicarbonates, such as di-tert-butyl dicarbonate, or dialkyl tricarbonates such as di-tert-butyl tricarbonate. One preferred aromatic carbonate is diphenyl carbonate. Preference is given to aliphatic carbonates, more particularly those in which the radicals comprise 1 to 5 C atoms, such as dimethyl carbonate, diethyl carbonate, di-n-propyl carbonate, di-n-butyl carbonate or diisobutyl carbonate, for example. Diethyl carbonate is especially preferred.

The hyperbranched polycarbonate preferably comprises an alcohol (B1) in polymerized form. The alcohol (B1) which has at least three hydroxyl groups is usually an aliphatic or aromatic alcohol, or a mixture or two or more different alcohols of this kind. The alcohol (B1) may be branched or unbranched, substituted or unsubstituted, and have 3 to 26 carbon atoms. It is preferably an aliphatic alcohol. Examples of compounds having at least three OH groups comprise glycerol, trimethylolmethane, trimethylolethane, trimethylolpropane, trimethylolbutane, 1,2,4-butanetriol, 1,2,3-hexanetriol, 1,2,4-hexanetriol, tris(hydroxymethyl)amine, tris(hydroxylethyl)amine, tris(hydroxypropyl)amine, pentaerythritol, diglycerol, triglycerol, polyglycerols, bis(trimethylolpropane), tris(hydroxymethyl) isocyanurate, tris(hydroxyethyl) isocyanurate, phloroglucinol, trihydroxytoluene, trihydroxydimethylbenzene, phloroglucides, hexahydroxybenzene, 1,3,5-benzenetrimethanol, 1,1,1-tris(4'-hydroxyphenyl)methane, 1,1,1-tris(4'-hydroxyphenyl)ethane, sugars, for example glucose, sugar derivatives, for example sorbitol, mannitol, diglycerol, threitol, erythritol, adonitol (ribitol), arabitol (lyxitol), xylitol, dulcitol (galactitol), maltitol, isomalt, or polyesterol.

Preferably, B1 is a trifunctional or higher-functionality polyetherol based on alcohols which have at least three OH groups, and $C_2$-$C_{24}$ alkylene oxide. The polyetherol comprises usually one to 30, preferably one to 20, more preferably one to 10 and most preferably one to eight molecules of ethylene oxide and/or propylene oxide and/or isobutylene oxide per hydroxyl group. The hyperbranched polycarbonate preferably comprises an alcohol (B1) which is a trifunctional or higher-functionality polyetherol based on alcohols which have at least three OH groups, and $C_3$-$C_{24}$ alkylene oxide. Suitable alcohols which have at least three OH groups are as described above, preferably glycerol, trimethylolethane, trimethylolpropane, 1,2,4-butanetriol, 1,2,3-hexanetriol, 1,2,4-hexanetriol, pentaerythritol, more preferably glycerol or trimethylolpropane. Preferred $C_3$-$C_{24}$ alkylene oxides include propylene oxide, butylene oxide, pentylene oxide and mixtures thereof, more preferably propylene oxide. The trifunctional or higher-functionality polyetherols usually comprise at least one to 30, preferably two to 30, more preferably three to 20 $C_3$-$C_{24}$ alkylene oxide molecules in polymerized form. A particularly preferred alcohol (B1) is a trifunctional polyetherol based on glycerol, trimethylolethane, trimethylolpropane, 1,2,4-butanetriol and/or pentaerythritol, and propylene oxide, where the polyetherol comprises at least three, preferably three to 30, more preferably three to 20, molecules of propylene oxide in polymerized form. Polyetherols (B1) are commercially available, e.g. under the Lupranol® marks, such as Lupranol® 3902 and 9319, from BASF SE.

In addition to the alcohol (B1), the polycarbonate may have a difunctional alcohol (B2) as a forming component, with the proviso that the mean OH functionality of all alcohols B used together is greater than 2. The alcohols (B1) and (B2) are referred to here together as (B). Suitable difunctional alcohols B2 include diethylene glycol, triethylene glycol, 1,2- and 1,3-propanediol, dipropylene glycol, tripropylene glycol, neopentyl glycol, 1,2-, 1,3- and 1,4-butanediol, 1,2-, 1,3- and 1,5-pentanediol, 1,6-hexanediol, 1,2- or 1,3-cyclopentanediol, 1,2-, 1,3- or 1,4-cyclohexanediol, 1,1-, 1,2-, 1,3- or 1,4-cyclohexanedimethanol, bis(4-hydroxycyclohexyl)methane, bis(4-hydroxycyclohexyl)ethane, 2,2-bis(4-hydroxycyclohexyl)propane, 1,1'-bis(4-hydroxyphenyl)-3,3,5-trimethylcyclohexane, resorcinol, hydroquinone, 4,4'-dihydroxybiphenyl, bis(4-hydroxyphenyl) sulfide, bis(4-hydroxyphenyl) sulfone, bis(hydroxymethyl)benzene, bis(hydroxylmethyl)toluene, bis(p-hydroxyphenyl)methane, bis(p-hydroxyphenyl)ethane, 2,2-bis(p-hydroxyphenyl)propane, 1,1-bis(p-hydroxyphenyl) cyclohexane, dihydroxybenzophenone, difunctional polyetherpolyols based on ethylene oxide, propylene oxide, butylene oxide or mixtures thereof, polytetrahydrofuran having a molar mass of 162 to 2000, polycaprolactone or polyesterols based on diols and dicarboxylic acids. Preferred difunctional alcohols (B2) are difunctional polyetherpolyols based on ethylene oxide, propylene oxide, butylene oxide or mixtures thereof, and polyesterols based on diols and dicarboxylic acids.

The diols serve for fine adjustment of the properties of the polycarbonate. If difunctional alcohols are used, the ratio of difunctional alcohols (B2) to the at least trifunctional alcohols (B1) is fixed by the person skilled in the art according to the desired properties of the polycarbonate. In general, the amount of the alcohol(s) (B2) is 0 to 50 mol % based on the total amount of all alcohols (B1) and (B2) together. The amount is preferably 0 to 35 mol %, more preferably 0 to 25 mol % and most preferably 0 to 10 mol %. In one preferred embodiment the polycondensate (a1) does not contain a difunctional alcohol (B2). In another embodiment the polycondensate (a1) comprises 0.5 to 10 mol % of a difunctional alcohol (B2).

The reaction of phosgene, diphosgene or triphosgene with the alcohol or alcohol mixture is generally effected with elimination of hydrogen chloride; the reaction of the carbonates with the alcohol or alcohol mixture to give the inventive high-functionality highly branched polycarbonate is effected with elimination of the monofunctional alcohol or phenol from the carbonate molecule.

After this reaction, i.e. without any further modification, the hyperbranched polycarbonate has high-functionality termination with hydroxyl groups and with carbonate groups or carbamoyl chloride groups. A high-functionality polycarbonate is understood in the context of this invention to mean a product which, as well as the carbonate groups which form the polymer skeleton, additionally has, in terminal or lateral position, at least three, preferably at least four and more preferably at least six functional groups. The functional groups are carbonate groups or carbamoyl chloride groups and/or OH groups. There is in principle no upper limit in the number of terminal or lateral functional groups, but products with a very high number of functional groups may have undesired properties, for example high viscosity or poor solubility. The polycarbonates of the present invention usually have not more than 500 terminal or lateral functional groups, preferably not more than 100 terminal or lateral functional groups.

In the preparation of the high-functionality polycarbonates, it is necessary to adjust the ratio of the compounds comprising OH groups to phosgene or carbonate (A) such that the resulting simplest condensation product (known hereinafter as condensation product (K)) comprises an average of either i) one carbonate or carbamoyl chloride group and more than one OH group or ii) one OH group and more than one carbonate or carbamoyl chloride group, preferably an average of either i) one carbonate or carbamoyl chloride group and at least two OH groups or ii) one OH group and at least two carbonate or carbamoyl chloride groups.

In a further embodiment, for fine adjustment of the properties of the polycarbonate, at least one difunctional carbonyl-reactive compound (A1) is used. This is understood to mean compounds which have two carbonate and/or carboxyl groups. Carboxyl groups may be carboxylic acids, carbonyl chlorides, carboxylic anhydrides or carboxylic esters, preferably carboxylic anhydrides or carboxylic esters and more preferably carboxylic esters. If such difunctional compounds (A1) are used, the ratio of (A1) to the carbonates or phosgenes (A) is fixed by the person skilled in the art according to the desired properties of the polycarbonate. In general, the amount of the difunctional compound(s) (A1) is 0 to 40 mol % based on the total amount of all carbonates/phosgenes (A) and compounds (A1) together. Preferably the amount is 0 to 35 mol %, more preferably 0 to 25 mol %, and very preferably 0 to 10 mol %. Examples of compounds (A1) are dicarbonates or dicarbamoyl chlorides of diols, examples of which are ethylene glycol, 1,2-propanediol, 1,3-propanediol, 1,1-dimethylethane-1,2-diol, 2-butyl-2-ethyl-1,3-propanediol, 2-ethyl-1,3-propanediol, 2-methyl-1,3-propanediol, neopentyl glycol, neopentyl glycol hydroxypivalate, 1,2-, 1,3- or 1,4-butanediol, 1,6-hexanediol, 1,10-decanediol, bis(4-hydroxycyclohexane)isopropylidene, tetramethylcyclobutanediol, 1,2-, 1,3- or 1,4-cyclohexanediol, cyclooctanediol, norbornanediol, pinanediol, decalindiol, 2-ethyl-1,3-hexanediol, 2,4-diethyloctane-1,3-diol, hydroquinone, bisphenol A, bisphenol F, bisphenol B, bisphenol S, 2,2-bis(4-hydroxycyclohexyl)propane, 1,1-, 1,2-, 1,3- and 1,4-cyclohexanedimethanol, and 1,2-, 1,3- or 1,4-cyclohexanediol. These compounds may be prepared, for example, by reacting said diols with an excess of, for example, the above-recited carbonates RO(CO)OR or chlorocarbonic esters, so that the dicarbonates thus obtained are substituted on both sides by groups RO(CO)—. A further possibility is to react the diols first with phosgene to give the corresponding chlorocarbonic esters of the diols, and then to react these esters with alcohols.

Further compounds (A1) are dicarboxylic acids, esters of dicarboxylic acids, preferably the methyl, ethyl, isopropyl, n-propyl, n-butyl, isobutyl, sec-butyl or tert-butyl esters, more preferably the methyl, ethyl or n-butyl esters. Examples of dicarboxylic acids of this kind are oxalic acid, maleic acid, fumaric acid, succinic acid, glutaric acid, adipic acid, sebacic acid, dodecanedioic acid, o-phthalic acid, isophthalic acid, terephthalic acid, azelaic acid, 1,4-cyclohexanedicarboxylic acid or tetrahydrophthalic acid, suberic acid, phthalic anhydride, tetrahydrophthalic anhydride, hexahydrophthalic anhydride, tetrachlorophthalic anhydride, endomethylenetetrahydrophthalic anhydride, glutaric anhydride, dimeric fatty acids, isomers thereof and hydrogenation products thereof.

The simplest structure of the condensation product (K), illustrated using, as example, the reaction of a carbonate (A) with a dialcohol or polyalcohol (B), produces the arrangement $XY_m$ or $Y_mX$, X being a carbonate or carbamoyl group, Y a hydroxyl group, and m generally an integer greater than 1 to 6, preferably greater than 1 to 4, more preferably greater than 1 to 3. The reactive group, which results as a single group, is generally referred to below as "focal group".

Where, for example, in the preparation of the simplest condensation product (K) from a carbonate and a dihydric alcohol, the molar reaction ratio is 1:1, then the result on average is a molecule of type XY, illustrated by the general formula (I).

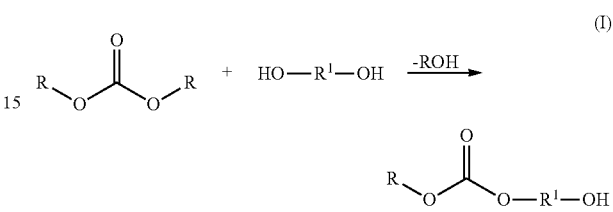

In the case of the preparation of the condensation product (K) from a carbonate and a trihydric alcohol with a molar reaction ratio of 1:1, the result on average is a molecule of type $XY_2$, illustrated by the general formula (II). The focal group here is a carbonate group.

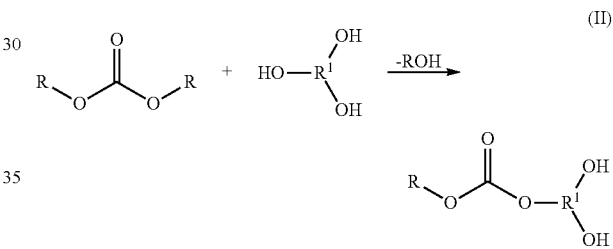

In the preparation of the condensation product (K) from a carbonate and a tetrahydric alcohol, again with the molar reaction ratio 1:1, the result on average is a molecule of type $XY_3$, illustrated by the general formula (III). The focal group here is a carbonate group.

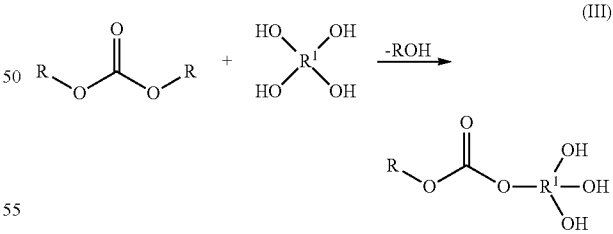

In the formulae (I) to (III) R is as defined at the outset and $R^1$ is an aliphatic or aromatic radical.

The condensation product (K) can also be prepared, for example, from a carbonate and a trihydric alcohol, illustrated by the general formula (IV), where the reaction ratio on a molar basis is 2:1. Here the result on average is a molecule of type $X_2Y$, the focal group here being an OH group. In the formula (IV) the definitions of R and $R^1$ are the same as above in formulae (I) to (III).

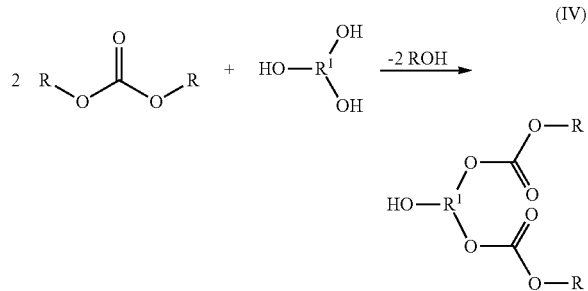

Where difunctional compounds, e.g., a dicarbonate or a diol, are additionally added to the components, this produces an extension of the chains, as illustrated for example in the general formula (V). The result again is on average a molecule of type $XY_2$, the focal group being a carbonate group.

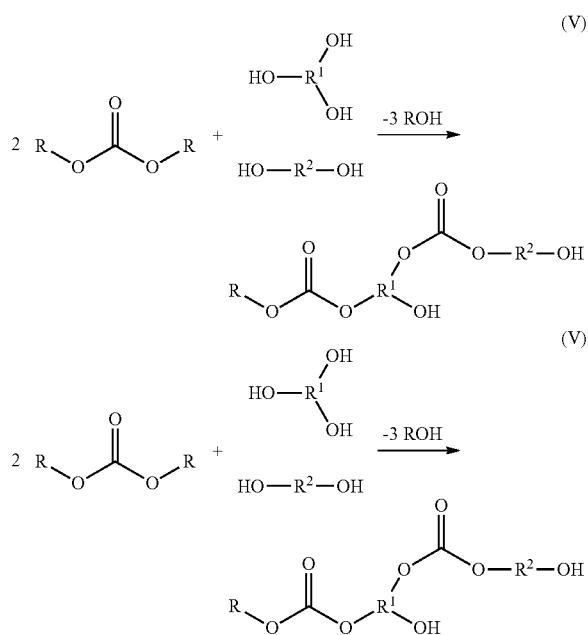

In formula (V) $R^2$ is an aliphatic or aromatic radical while R and $R^1$ are defined as described above.

It is also possible to use two or more condensation products (K) for the synthesis. In this case it is possible on the one hand to use two or more alcohols and/or two or more carbonates. Furthermore, through the choice of the ratio of the alcohols and carbonates or phosgenes used, it is possible to obtain mixtures of different condensation products with different structure. This may be exemplified taking, as example, the reaction of a carbonate with a trihydric alcohol. If the starting products are used in a 1:1 ratio, as depicted in (II), a molecule $XY_2$ is obtained. If the starting products are used in a 2:1 ratio, as illustrated in (IV), the result is a molecule $X_2Y$. With a ratio between 1:1 and 2:1 a mixture of molecules $XY_2$ and $X_2Y$ is obtained.

Typical reaction conditions for the reaction of (A) with (B) to form the condensation product (K) are set out below:

The stoichiometry of components (A) and (B) is generally chosen such that the resultant condensation product (K) contains either one carbonate or carbamoyl chloride group and more than one OH group, or one OH group and more than one carbonate or carbamoyl chloride group.

This is achieved in the first case by a stoichiometry of 1 mol of carbonate groups: >2 mol of OH groups, for example, a stoichiometry of 1:2.1 to 8, preferably 1:2.2 to 6, more preferably 1:2.5 to 4, and very preferably 1:2.8 to 3.5. In the second case it is achieved by a stoichiometry of more than 1 mol of carbonate groups: <1 mol of OH groups, for example, a stoichiometry of 1:0.1 to 0.48, preferably 1:0.15 to 0.45, more preferably 1:0.25 to 0.4, and very preferably 1:0.28 to 0.35.

The temperature ought to be sufficient for the reaction of the alcohol with the corresponding carbonyl component. For the reaction with a phosgene a sufficient temperature is generally from −20° C. to 120° C., preferably 0 to 100° C., and more preferably 20 to 80° C. When a carbonate is used the temperature should be 60 to 280° C., preferably 80 to 250° C., more preferably 100 to 250° C., and very preferably 120 to 250° C.

Preparation takes place usually in a pressure range from 0.1 mbar to 20 bar, preferably at 1 mbar to 5 bar, in reactors or reactor cascades, which are operated batchwise, semi-batchwise or continuously.

Solvents contemplated include aromatic and/or (cyclo) aliphatic hydrocarbons and mixtures thereof, halogenated hydrocarbons, ketones, esters, and ethers, preferably butyl acetate, dimethylformamide, dimethylacetamide, dimethyl sulfoxide, methoxypropyl acetate, isobutyl methyl ketone, 2-butanone, aromatic hydrocarbons (such as Solvesso® products), cyclohexane, chlorobenzene, and xylene. A preferred embodiment is to carry out the reaction without solvent.

The order in which the individual components are added is generally of minor importance. As a general rule it is sensible to introduce the excess component of the two reaction partners first and to add the deficit component. Alternatively it is likewise possible to mix the two components with one another before the beginning of reaction and then to heat this mixture to the requisite reaction temperature.

The simple condensation products (K) described exemplarily in formulae (I)-(V) undergo in accordance with the invention preferably immediate intermolecular further reaction to form high-functionality polycondensation products, referred to below as polycondensation products (P). The reaction to give the condensation product (K) and to give the polycondensation product (P) takes place usually at a temperature of 0 to 300° C., preferably 0 to 250° C., more preferably at 60 to 250° C., and very preferably at 80 to 250° C., in bulk (without solvent) or in solution. In this context it is possible generally to use any solvents which are inert toward the respective reactants. Preference is given to using organic solvents, such as those mentioned above, for example, and more preferably decane, dodecane, cyclohexane, benzene, toluene, chlorobenzene, xylene, dimethylformamide, dimethylacetamide, dimethyl sulfoxide or solvent naphtha. In one preferred embodiment the condensation reaction is carried out in bulk. The monofunctional alcohol or the phenol which is liberated during the reaction, ROH, can be removed from the reaction equilibrium in order to accelerate the reaction, such removal taking place, for example, by distillative means, if desired under reduced pressure.

The separation of the alcohol or phenol can also be assisted by passing through the reaction mixture a stream of gas which is substantially inert under the reaction conditions (i.e., stripping), such as, for example, nitrogen, steam, carbon dioxide, or else by passing through the mixture an oxygen-containing gas, such as atmospheric air or lean air, for example. If distillative removal is intended, it is advisable as a general rule to use carbonates which during the reaction give off alcohols or phenols ROH having a boiling point of less than 140° C. under the prevailing pressure. Alternatively the alcohols liberated may be removed by azeotropic distillation using azeotrope formers (e.g., toluene, xylene, chlorobenzene, cyclohexane) or by application of a vacuum, such removal supporting the formation of the polycondensate.

To accelerate the reaction it is also possible to add catalysts or catalyst mixtures. Suitable catalysts are compounds which catalyze esterification or transesterification reactions, examples being alkali metal hydroxides, alkali metal carbonates, alkali metal hydrogen carbonates, preferably of sodium, of potassium or of cesium, tertiary amines, guanidines, ammonium compounds, phosphonium compounds, organoaluminum, organotin, organozinc, organotitanium, organozir-conium or organobismuth compounds, and also catalysts of the kind known as double metal cyanide (DMC) catalysts, as described, for example, in DE 10138216 or in DE 10147712. Preference is given to using potassium hydroxide, potassium carbonate, potassium hydrogen carbonate, diazabicyclooctane (DABCO), diazabicyclononene (DBN), diazabicycloundecene (DBU), imidazoles, such as imidazole, 1-methylimidazole or 1,2-dimethylimidazole, titanium tetrabutoxide, titanium tetraisopropoxide, dibutyltin oxide, dibutyltin dilaurate, tin dioctoate, zirconium acetylacetonate, or mixtures thereof. The catalyst is generally added in an amount of 50 to 10 000 ppm by weight, preferably of 100 to 5000 ppm by weight, based on the amount of alcohol or alcohol mixture employed. It may possibly be necessary to predissolve the catalyst in small amounts of a suitable solvent.

Furthermore it is also possible, either by adding the appropriate catalyst and/or by choosing a suitable temperature, to control the intermolecular polycondensation reaction. In addition the average molecular weight of the polymer (P) can be adjusted via the composition of the starting components and via the residence time.

The condensation products (K) and the polycondensation products (P), which have been prepared at an elevated temperature, are stable at room temperature usually for a relatively long period of time, for example, for at least 6 weeks, without displaying turbidities, precipitations and/or any increase in viscosity. In view of the nature of the condensation products (K) it is possible that the condensation reaction may result in polycondensation products (P) having different structures, with branches but no crosslinks. Furthermore, the polycondensation products (P) ideally contain either a carbonate or carbamoyl chloride focal group and more than two OH groups, or else an OH focal group and more than two carbonate or carbamoyl chloride groups. The number of reactive groups depends on the nature of the condensation products (K) employed and on the degree of polycondensation.

For example, a condensation product (K) of the general formula (II) may react by triple intermolecular condensation to form two different polycondensation products (P), which are reproduced in general formulae (VI) and (VII).

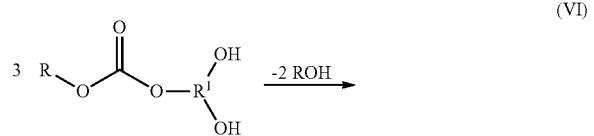

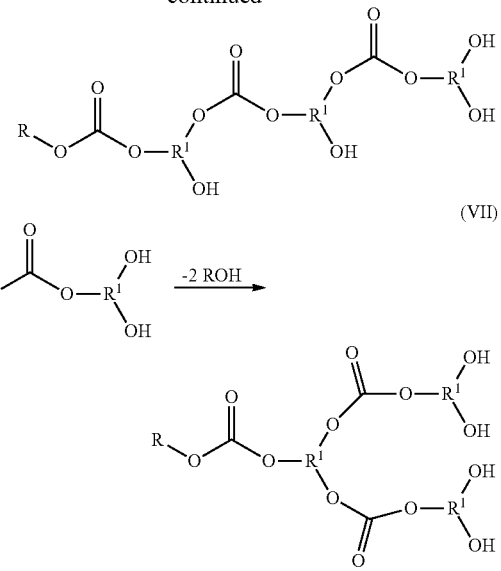

R and R¹ in formulae (VI) and (VII) are as defined above.

To terminate the intermolecular polycondensation reaction there are a variety of possibilities. By way of example the temperature can be lowered to a range in which the reaction comes to a standstill and the product (K) or the polycondensation product (P) is stable on storage. This is generally the case at below 60° C., preferably below 50° C., more preferably below 40° C., and very preferably at room temperature. Furthermore, the catalyst can be deactivated: in the case of basic catalysts, for example, by adding an acidic component, a Lewis acid for example, or an organic or inorganic protic acid. A further possibility is to arrest the reaction by dilution with a precooled solvent. This is particularly preferred when it is necessary to adapt the viscosity of the reaction mixture by adding solvent.

In a further embodiment, as soon as the intermolecular reaction of the condensation product (K) gives a polycondensation product (P) having the desired degree of polycondensation, the reaction can be arrested by adding to the product (P) a product having groups that are reactive toward the focal group of (P). For instance, in the case of a carbonate or carbamoyl focal group, a mono-, di- or polyamine, for example, can be added. In the case of a hydroxyl focal group, the product (P) can have added to it, for example, a mono-, di- or polyisocyanate, a compound comprising epoxide groups, or an acid derivative which is reactive with OH groups.

As a result of the aforementioned setting of the reaction conditions and, if desired, as a result of the choice of suitable solvent, the products of the invention can be processed further following preparation, without additional purification. If necessary, the reaction mixture can be subjected to decoloring, by means for example of treatment with activated carbon or metal oxides, such as alumina, silica, magnesium oxide, zirconium oxide, boron oxide or mixtures thereof, in amounts for example of 0.1%-50%, preferably 0.5% to 25%, more preferably 1%-10%, by weight, at temperatures of, for example, 10 to 100° C., preferably 20 to 80° C., and more preferably 30 to 60° C. If desired it is also possible to filter the reaction mixture in order to remove any precipitates present. In a further preferred embodiment the product is stripped, i.e., freed from volatile compounds of low molecular weight. For this purpose, after the desired degree of conversion has been reached, the catalyst can be optionally deactivated and the volatile constituents of low molecular weight, such as monoalcohols, phenols, carbonates, hydrogen chloride or volatile oligomeric or cyclic compounds, can be removed by distillation, if desired accompanied by introduction of a gas, preferably nitrogen, carbon dioxide or air, if desired under reduced pressure.

The hyperbranched polycarbonates obtainable as described above generally have a glass transition temperature of less than 50° C., preferably less than 30 and more preferably less than 10° C. The OH number is usually at least 30 mg KOH/g, preferably between 50 and 500 mg/g. The weight-average molar weight $M_w$ is usually between 1000 and 150 000, preferably from 1500 to 100 000 g/mol, the number-average molar weight $M_n$ between 500 and 50 000, preferably between 1000 and 40 000 g/mol. The hyperbranched polycarbonate is usually not soluble or dispersible in water, i.e., it is not possible to prepare a clear (i.e., devoid of particles visible to the naked eye) aqueous solution or dispersion.

Polyesters (a2)

In a further preferred embodiment the hyperbranched polymer is a hyperbranched polyester.

In a known manner, the polyesters have ester linkages. In one preferred embodiment, the polymers comprise, as structural units, in each case at least one hydrophobic dicarboxylic acid unit and at least one trifunctional alcohol. They may additionally comprise further structural units. The hyperbranched polyester is usually soluble or dispersible in water, which means that it is possible to prepare a clear (i.e. without particles discernible to the naked eye) aqueous solution or dispersion.

The polyester is preferably based on a hydrophobic dicarboxylic acid which is an aliphatic $C_{10}$-$C_{32}$ dicarboxylic acid, a dicarboxylic acid having a polyisobutylene group and/or a succinic acid unit having a $C_3$-$C_{40}$ group. In a preferred embodiment, the hydrophobic dicarboxylic acid is an aliphatic $C_{10}$-$C_{32}$ dicarboxylic acid. In a further preferred embodiment, the hydrophobic dicarboxylic acid is a dicarboxylic acid having a polyisobutylene group. In a further preferred embodiment, the hydrophobic dicarboxylic acid is a succinic acid unit having a $C_3$-$C_{40}$ group. In a further preferred embodiment, the hydrophobic dicarboxylic acid is a dicarboxylic acid having a polyisobutylene group and/or a succinic acid unit having a $C_3$-$C_{40}$ group.

A suitable hydrophobic dicarboxylic acid is an aliphatic $C_{10}$-$C_{32}$ dicarboxylic acid. Preference is given to sebacic acid, a,w-undecanedicarboxylic acid, a,w-dodecanedicarboxylic acid, tridecanedicarboxylic acid (brassylic acid). Sebacic acid is especially preferred.

Another suitable hydrophobic dicarboxylic acid is a dicarboxylic acid having a polyisobutylene group (also referred to hereinafter as "PIB diacid"). In this connection, a "dicarboxylic acid having a polyisobutylene group" has at least two dicarboxylic acid groups, at least two dicarboxylic ester groups or at least one dicarboxylic anhydride group (it preferably has one dicarboxylic anhydride group). Such PIB diacids are obtainable by reacting polyisobutylene with an enophile. In a preferred embodiment, the products are 1:1 (mol/mol) reaction products of an ene reaction of a polyisobutylene and of the enophile. The PIB diacid is prepared by the processes known to those skilled in the art and preferably as described in German laid-open specifications DE-A 195 19 042, preferably from page 2 line 39 to page 4 line 2 and more preferably from page 3 line 35 to 58, and DE-A 43 19 671, preferably from page 2 line 30 to line 68, and DE-A 43 19 672, preferably from page 2 line 44 to page 3 line 19, described processes for reacting polyisobutylenes with enophiles. The polyisobutylenes are preferably those which have to an extent of at least 60 mol % end groups formed from vinyl isomer and/or vinylidene isomer.

To synthesize the hyperbranched polyesters, it is possible to use succinic acid substituted in the manner described. The succinic acid may preferably be used, however, in the form of activated derivatives, especially in the form of halides, esters or anhydrides.

Derivatives are especially the relevant anhydrides in monomeric or else polymeric form, mono- or dialkyl esters, preferably mono- or di-$C_1$-$C_4$-alkyl esters, more preferably mono- or dimethyl esters or the corresponding mono- or diethyl esters, and also mono- and divinyl esters and mixed esters, preferably mixed esters with different $C_1$-$C_4$-alkyl components, more preferably mixed methyl ethyl esters.

Particular preference is given to using succinic anhydrides as the starting material. In addition to the high reactivity of the anhydrides, the use of the anhydrides has the advantage that alkenylsuccinic anhydrides can be prepared in a particularly simple and inexpensive manner by reacting maleic anhydrides with olefins which have a hydrogen atom in the allyl position (the so-called ene reaction). Reaction of linear a-olefins can provide alkenylsuccinic anhydrides with n-alkenyl radicals; isomerized olefins with nonterminal double bonds give rise to succinic anhydrides substituted by isoalkenyl radicals. The olefins used may also be reactive oligo- or polyolefins, though reactive polyisobutenes are preferably not used. The preparation of alkenylsuccinic anhydrides (also known as ASA) by means of the ene reaction is described in detail, for example, in WO 97/23474 or DE 195 19 042 and the literature cited therein.

Succinic anhydrides substituted by alkenyl groups which are used with preference are n- or isohexenylsuccinic anhydride, n- or isoheptenylsuccinic anhydride, n- or isooctenylsuccinic anhydride, n- or isooctadienylsuccinic anhydride, n- or isononenylsuccinic anhydride, n- or isodecenylsuccinic anhydride, n- or isododecenylsuccinic anhydride (DDSA), n- or isotetradecenylsuccinic anhydride, n- or isohexadecenylsuccinic anhydride, n- or isooctadecenylsuccinic anhydride, tetrapropenylsuccinic anhydride, 2-dodecenyl-3-tetradecenylsuccinic anhydride. It will be appreciated that it is also possible to use mixtures of different substituted anhydrides.

Particularly preferred products are n- or isooctenylsuccinic anhydride, n- or isododecenylsuccinic anhydride (DDSA), n- or isotetradecenylsuccinic anhydride, n- or isohexadecenylsuccinic anhydride, n- or isooctadecenylsuccinic anhydride, tetrapropenylsuccinic anhydride or mixtures of the products mentioned. Very particular preference is given to n- or isohexadecenylsuccinic anhydride, n- or isooctadecenylsuccinic anhydride, or mixtures thereof.

The alkenylsuccinic acids or derivatives or mixtures thereof can also be used in a mixture with alkylsuccinic acids or derivatives thereof.

To prepare the hyperbranched polyesters, at least one hydrophobic dicarboxylic acid is reacted with at least one trifunctional alcohol, the ratio of the reactive groups in the reaction mixture being selected such that a molar ratio of OH groups to carboxyl groups or derivatives thereof of 5:1 to 1:5, preferably of 4:1 to 1:4, more preferably of 3:1 to 1:3 and most preferably of 2:1 to 1:2 is established. When mixtures of hydrophobic aliphatic $C_{10}$-$C_{32}$ dicarboxylic acids and/or dicarboxylic acids having polyisobutylene groups and/or succinic acid units having a $C_3$-$C_{40}$ group are used, the stoichiometry of OH groups to carboxyl groups is usually maintained as described above.

Trifunctional alcohols are understood to mean alcohols with at least three alcohol groups. Suitable trifunctional alcohols are glycerol, trimethylolethane, trimethylolpropane, bis(trimethylolpropane), pentaerythritol, or an alkoxylated, preferably ethoxylated or propoxylated derivative thereof. It will be appreciated that it is also possible to use mixtures of a plurality of different trifunctional alcohols. Preferred trifunctional alcohols are glycerol, trimethylolpropane and pentaerythritol. Very particular preference is given to glycerol and trimethylolpropane.

Alkoxylated derivatives of glycerol, trimethylolethane, trimethylolpropane, bis(trimethylolpropane), pentaerythritol can be obtained in a manner known in principle by alkoxylating the alcohols with alkylene oxide, such as ethylene oxide, propylene oxide, butylene oxide, and/or pentylene oxide. The mixed alkoxylated polyetherols may be copolymers in which, for example, different alkylene oxide units are distributed randomly in the chain, or they may be block copolymers.

The alkoxylated derivative of glycerol, trimethylolethane, trimethylolpropane, bis(trimethylolpropane) or pentaerythritol is preferably alkoxylated with 1.1 to 20 alkylene oxide units, preferably ethylene oxide and/or propylene oxide units. The alkoxylated derivative of glycerol, trimethylolpropane or pentaerythritol is most preferably alkoxylated with 1.1 to 20 propylene oxide units.

In addition to the components mentioned—In further embodiments it is possible to use further components to synthesize the hyperbranched polymers used in accordance with the invention. Such components can be used to influence the properties of the polymers and adjust them optimally for the desired purpose.

For instance, it is possible to use further di- or polyfunctional carboxylic acids. Examples of further carboxylic acids comprise malonic acid, succinic acid, glutaric acid, adipic acid, 1,2-, 1,3- or 1,4-cyclohexanedicarboxylic acid (hexahydrophthalic acids), phthalic acid, isophthalic acid, terephthalic acid or derivatives thereof, especially the anhydrides or esters thereof. The amount of such further carboxylic acids should, however, generally not exceed 50 mol % based on the amount of all carboxylic acids used (i.e. sum of hydrophobic dicarboxylic acids and further di- or polyfunctional carboxylic acids) together.

In addition, as well as the trifunctional alcohols, it is also possible to use difunctional aliphatic, cycloaliphatic, araliphatic or aromatic diols. The suitable selection of dihydric alcohols can influence the properties of the polyesters. Examples of suitable diols are ethylene glycol, 1,2-propanediol, 1,3-propanediol, 1,4-butanediol, 1,5-pentanediol, 1,6-hexanediol, 1,8-octanediol, 1,2-, 1,3- and 1,4-cyclohexanediol, 1,3- and 1,4-bis(hydroxymethyl)cyclohexane, and also diethylene glycol, triethylene glycol, dipropylene glycol, tripropylene glycol, polyethylene glycols $HO(CH_2CH_2O)_n$—H or polypropylene glycols $HO(CH[CH_3]CH_2O)_n$—H, where n is an integer and n is 4, polyethylene-polypropylene glycols, where the sequence of the ethylene oxide or propylene oxide units may be blockwise or random, or polytetramethylene glycols, preferably up to a molar mass of 5000 g/mol. The dihydric alcohols may optionally also comprise further functionalities, for example carbonyl, carboxyl, alkoxycarbonyl or sulfonyl functions, for example dimethylolpropionic acid or dimethylolbutyric acid, and the $C_1$-$C_4$-alkyl esters thereof, glyceryl monostearate or glyceryl monooleate. The amount of such further dihydric alcohols should, however, generally not exceed 50 mol % based on the amount of all alcohols used (i.e. sum of trifunctional alcohol and difunctional diol). The amount of dihydric alcohols is preferably not more than 30 mol %, more preferably not more than 20 mol %. Most preferably, only the trifunctional alcohols are used.

In a further preferred embodiment, the polyester (a2) is based on a tri- or polycarboxylic acid such as citric acid. Citric acid is particularly preferred. Such polyesters are disclosed e.g. in WO 2012/028496 and WO 2014/016148.

According to the invention, citric acid is understood as meaning citric acid anhydrate and also the hydrates of citric acid, such as, for example, citric acid monohydrate.

According to the invention, suitable polyalcohols are alcohols with at least two hydroxyl groups and up to six hydroxyl groups. Preferably, diols or triols or mixtures of different diols and/or triols are contemplated. Suitable polyalcohols are, for example, polyetherols. The polyetherols can be obtained by reaction with ethylene oxide, propylene oxide and/or butylene oxide. In particular, polyetherols based on ethylene oxide and/or propylene oxide are suitable. It is also possible to use mixtures of such polyetherols.

Suitable diols are, for example ethylene glycol, propane-1,2-diol, propane-1,3-diol, butane-1,2-diol, butane-1,3-diol, butane-1,4-diol, butane-2,3-diol, pentane-1,2-diol, pentane-1,3-diol, pentane-1,4-diol, pentane-1,5-diol, pentane-2,3-diol, pentane-2,4-diol, hexane-1,2-diol, hexane-1,3-diol, hexane-1,4-diol, hexane-1,5-diol, hexane-1,6-diol, hexane-2,5-diol, heptane-1,2-diol, 1,7-heptanediol, 1,8-octanediol, 1,2-octanediol, 1,9-nonanediol, 1,2-decandiol, 1,10-decandiol, 1,2-dodecandiol, 1,12-dodecandiol, 1,5-hexadiene-3,4-diol, 1,2- and 1,3-cyclopentanediols, 1,2-, 1,3- and 1,4-cyclohexanediols, 1,1-, 1,2-, 1,3- and 1,4-bis(hydroxymethyl)cyclohexanes, 1,1-, 1,2-, 1,3- and 1,4-bis(hydroxyethyl)cyclohexanes, neopentyl glycol, (2)-methyl-2,4-pentanediol, 2,4-dimethyl-2,4-pentanediol, 2-ethyl-1,3-hexanediol, 2,5-dimethyl-2,5-hexanediol, 2,2,4-trimethyl-1,3-pentanediol, pinacol, diethylene glycol, triethylene glycol, dipropylene glycol, tripropylene glycol, polyethylene glycols $HO(CH_2CH_2O)_n$—H or polypropylene glycols $HO(CH[CH_3]CH_2O)_n$—H, where n is an integer and n≥4, polyethylene polypropylene glycols, where the sequence of the ethylene oxide of the propylene oxide units can be blockwise or random, polytetramethylene glycols, preferably up to a molecular weight up to 5000 g/mol, poly-1,3-propanediols, preferably with a molecular weight up to 5000 g/mol, polycaprolactones or mixtures of two or more representatives of the above compounds. For example, one to six, preferably one to four, particularly preferably one to three, very particularly preferably one to two and in particular one diol can be used. Here, one or both hydroxyl groups in the diols specified above can be substituted by SH groups. Diols preferably used are ethylene glycol, 1,2-propanediol, 1,3-propanediol, 1,4-butanediol, 1,5-pentanediol, 1,6-hexanediol, 1,8-octanediol, 1,2-, 1,3- and 1,4-cyclohexanediol, 1,3- and 1,4-bis(hydroxymethyl)cyclohexane, and diethylene glycol, triethylene glycol, dipropylene glycol, tripropylene glycol and polyethylene glycols with an average molecular weight between 200 and 1000 g/mol.

The dihydric polyalcohols can optionally also comprise further functionalities such as, for example, carbonyl, carboxyl, alkoxycarbonyl or sulfonyl, such as, for example, dimethylolpropionic acid or dimethylolbutyric acid, and $C_1$-$C_4$-alkyl esters thereof, although the alcohols preferably have no further functionalities.

Preferred diols are ethylene glycol, diethylene glycol and polyethylene glycol with an average molecular weight between 200 and 1000 g/mol.

Suitable triols or higher-functional polyalcohols are, for example, glycerol, trimethylolmethane, trimethylolethane, trimethylolpropane, bis(trimethylolpropane), trimethylolbutane, trimethylolpentane, 1,2,4-butanetriol, 1,2,6-hexanetriol, tris(hydroxymethyl)amine, tris(hydroxyethyl)amine, tris(hydroxypropyl)amine, pentaerythritol, diglycerol, triglycerol or higher condensation products of glycerol, di(trimethylolpropane), di(pentaerythritol), tris(hydroxymethyl) isocyanurate, tris(hydroxyethyl) isocyanurate (THEIC), tris(hydroxypropyl) isocyanurate and N-[1,3-bis(hydroxymethyl)-2,5-dioxo-4-imidazolidinyl]-N,N'-bis(hydroxymethyl)urea.

Preferred triols are trimethylolpropane, trimethylolethane, glycerol, diglycerol and triglycerol, and polyetherols thereof based on ethylene oxide and/or propylene oxide. Also suitable are furthermore sugars or sugar alcohols, such as, for example, glucose, fructose or sucrose, sugar alcohofs such as e.g. sorbitol, mannitol, threitol, erythritol, adonitol (ribitol), arabitol (lyxitol), xylitol, dulcitol (galactitol), maltitol, isomalt, or inositol.

Also suitable are tri- or higher-functional polyetherols based on tri- or higher-functional alcohols which are obtained by reaction with ethylene oxide, propylene oxide and/or butylene oxide, or mixtures of such reaction products.

It is also possible to use mixtures of at least trifunctional polyalcohols. For example, one to six, preferably one to four, particularly preferably one to three, very particularly preferably one to two and in particular one at least trifunctional alcohol can be used.

In this connection, ethylene glycol, 1,2-propanediol, 1,3-propanediol, 1,4-butanediol, 1,5-pentanediol, 1,6-hexanediol, and diethylene glycol, triethylene glycol, dipropylene glycol, tripropylene glycol, polyethylene glycol with an average molecular weight between 200 and 1000 g/mol, glycerol, diglycerol, triglycerol, trimethylolpropane, trimethylolethane, di(trimethylolpropane), 1,2,4-butanetriol, 1,2,6-hexanetriol, pentaerythritol, sucrose, sorbitol or glucaric acid, and polyetherols thereof based on ethylene oxide and/or propylene oxide, or a mixture thereof are preferred as component B.

Particular preference is given to diethylene glycol or polyethylene glycol with an average molecular weight between 200 and 1000 g/mol, trimethylolpropane, glycerol or diglycerol, triglycerol, and polyetherols thereof based on ethylene oxide and/or propylene oxide, or a mixture thereof.

In addition to the citric acid, further carboxylic acids, in particular saturated dicarboxylic acids, can be condensed in, in which case the fraction of further polycarboxylic acids should be at most 30 mol % compared with the amount of citric acid used. Preferably, the polycarboxylic acids of component C comprise no sulfonate groups.

Suitable saturated dicarboxylic acids are, for example, aliphatic dicarboxylic acids, such as oxalic acid, malonic acid, succinic acid, glutaric acid, adipic acid, pimelic acid, suberic acid, azeleic acid, sebacic acid, undecane-α,ω-dicarboxylic acid, dodecane-α,ω-dicarboxylic acid, cis- and trans-cyclohexane-1,2-dicarboxylic acid, cis- and trans-cyclohexane-1,3-dicarboxylic acid, cis- and trans-cyclohexane-1,4-dicarboxylic acid, cis- and trans-cyclopentane-1,2-dicarboxylic acid, cis- and trans-cyclopentane-1,3-dicarboxylic acid. The specified saturated dicarboxylic acids can also be substituted with one or more radicals selected from $C_1$-$C_2$O-alkyl groups, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, 2-ethylhexyl, trimethylpentyl, n-nonyl, n-decyl, n-dodecyl, n-tetradecyl, n-hexadecyl, n-octadecyl, or n-eicosyl, $C_2$-$C_{20}$-alkenyl groups, for example butenyl, hexenyl, octenyl, decenyl, dodecenyl, tetradecenyl, hexadecenyl, octadecenyl or eicosenyl, $C_3$-$C_{12}$-cycloalkyl groups, for example cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl;

alkylene groups such as methylene or ethylidene or $C_6$-$C_{14}$-aryl groups such as, for example, phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl.

Exemplary representatives of substituted dicarboxylic acids or derivatives thereof which may be mentioned are: 2-methylmalonic acid, 2-ethylmalonic acid, 2-phenylmalonic acid, 2-methylsuccinic acid, 2-ethylsuccinic acid, 2-phenylsuccinic acid, 3,3-dimethylglutaric acid, dodecenylsuccinic acid, hexadecenylsuccinic acid and octadecenylsuccinic acid. The dicarboxylic acids can either be used as they are or in the form of derivatives.

Derivatives are preferably understood as meaning the relevant anhydrides in monomeric or else polymeric form, mono- or dialkyl esters, preferably mono- or di-$C_1$-$C_4$-alkyl esters, particularly preferably mono- or dimethyl esters or the corresponding mono- or diethyl esters, as well as mixed esters, preferably mixed esters with different $C_1$-$C_4$-alkyl components, particularly preferably mixed methyl ethyl esters.

Among these, preference is given to the anhydrides and the mono- or dialkyl esters, particularly preferably the anhydrides and the mono- or di-$C_1$-$C_4$-alkyl esters and very particularly preferably the anhydrides.

Within the context of this specification, $C_1$-$C_4$-alkyl means methyl, ethyl, isopropyl, n-propyl, n-butyl, isobutyl, sec-butyl and tert-butyl, preferably methyl, ethyl and n-butyl, particularly preferably methyl and ethyl and very particularly preferably methyl.

Particularly preferably, malonic acid, succinic acid, glutaric acid, adipic acid, sebacic acid, octadecenylsuccinic anhydride, 1,2-, 1,3- or 1,4-cyclohexanedicarboxylic acids (hexahydrophthalic acids as cis or trans compounds or mixtures thereof) are used.

Further preferred dicarboxylic acids are glucaric acid and tartaric acid.

The amount of dicarboxylic acid is not more than 30 mol % compared with the amount of citric acid used, preferably not more than 20%, very particularly preferably not more than 15%.

Suitable components D are alkyl- or alkenylcarboxylic acids, such as, for example, long-chain, linear or branched carboxylic acids having 6 to 30 carbon atoms, preferably 8 to 22 carbon atoms, in particular 10 to 18 carbon atoms, in the alkyl or alkenyl radical, such as octanoic acid, nonanoic acid, decanoic acid, undecanoic acid, dodecanoic acid, tridecanoic acid, tetradecanoic acid, hexadecanoic acid, arachic acid, behenic acid, palmitoleic acid, stearic acid, oleic acid, linoleic acid, linolenic acid, arachidonic acid or Li, Na, K, Cs, Ca or ammonium salts thereof. It is also possible to use mixtures.

Preferably, oleic acid, palmitic acid, linoleic acid, stearic acid, lauric acid and ricinoleic acid are used.

The alkyl- or alkenylcarboxylic acids can also be used in the form of their carboxylic acid alkyl esters. Preference is given to using the methyl esters.

Suitable long-chain alcohols are, for example, linear or branched alcohols having 6 to 30 carbon atoms, preferably 8 to 22 carbon atoms, in particular 10 to 18 carbon atoms in the linear or branched alkyl radical, such as octan-1-ol, decan-1-ol, lauryl alcohol, myristyl alcohol, cetyl alcohol, stearyl alcohol, eicosanol, behenyl alcohol, 9-hexadecen-1-ol and 9-octadecen-1-ol. Preference is given to using lauryl alcohol and stearyl alcohol.

Exemplary representatives of alkyl- or alkenylamines which may be mentioned are:
linear or branched alkylamines having 6 to 30 carbon atoms, preferably 8 to 22 carbon atoms, in particular 10 to 18 carbon atoms, in the linear or branched alkyl radical, such as hexylamine, octylamine, nonylamine, decylamine, dodecylamine, tetradecylamine, hexadecylamine, octadecylamine and mixtures thereof.

Suitable long-chain isocyanates are linear or branched isocyanates having 6 to 30 carbon atoms, preferably 8 to 22 carbon atoms, in particular 10 to 18 carbon atoms, in the linear or branched alkyl radical, such as octyl isocyanate, dodecyl isocyanate, stearic isocyanate and mixtures thereof.

The molar ratio of (component A+component B) to component D is preferably 10:0.1 to 0.5:0.1, particularly preferably 5:0.1 to 1:0.1.

The present invention further provides hydrophobicized branched polyesters as described above and the process for the preparation thereof.

The conversion of all components of the hyperbranched polyester (a2) can be performed in the presence or absence of a solvent. Suitable solvents are, for example, hydrocarbons such as paraffins, aromatics, ethers and ketones. Preferably, the reaction is, however, performed free of solvent.

The reaction is effected generally at elevated temperatures, for example 30 to 250° C., especially 80 to 220° C. and more preferably 80 to 180° C.

The water or the alcohols formed during the polymerization (polycondensation) should be removed from the reaction medium by means of suitable measures. The reaction can be effected, for example, in the presence of a water-withdrawing agent as an additive which is added at the start of the reaction. Suitable examples are molecular sieves, especially 4 Å molecular sieve, anhydrous $MgSO_4$ or anhydrous $Na_2SO_4$. In addition, water or alcohols formed during the reaction can be distilled off. This can also be done by means of a suitable entraining agent using a water separator. The distillation can preferably be effected under reduced pressure, for example at a pressure of 1 mbar to 500 mbar.

The reaction can be performed in the absence of catalysts. Preference is given, however, to working in the presence of at least one catalyst. The catalysts are preferably acidic inorganic, organometallic or organic catalysts, or mixtures of a plurality of acidic inorganic, organometallic or organic catalysts. It is also possible to use enzymes as catalysts, although the use thereof is less preferred.

Acidic inorganic catalysts for the purposes of the present invention are for example sulfuric acid, sulfates and hydrogen sulfates, such as sodium hydrogen sulfate, phosphoric acid, phosphonic acid, hypophosphorous acid, aluminum sulfate hydrate, alum, acidic silica gel (pH≤6, especially ≤5) and acidic aluminum oxide. Further acidic inorganic catalysts which can be used include, for example, aluminum compounds of the general formula $Al(OR^1)_3$ and titanates of the general formula $Ti(OR^1)_4$, it being possible for the radicals $R^1$ to be identical or different in each case and to be selected independently of one another from $C_1$-$C_{20}$ alkyl radicals, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, 2-ethylhexyl, n-nonyl, n-decyl, n-dodecyl, n-hexadecyl or n-octadecyl, for example; $C_3$-$C_{12}$ cycloalkyl radicals, such as cyclopropyl, cyclobutyl, cyclopentyl, cyclohexyl, cycloheptyl, cyclooctyl, cyclononyl, cyclodecyl, cycloundecyl and cyclododecyl, for example; preferably cyclopentyl, cyclohexyl and cycloheptyl. The radicals $R^1$ in $Al(OR^1)_3$ and/or $Ti(OR^1)_4$ are preferably each identical and selected from n-butyl, isopropyl and 2-ethylhexyl.

Preferred acidic organometallic catalysts are chosen for example from dialkyltin oxides $R^1_2$ SnO or dialkyltin diesters $R^1_2 Sn(OR^2)_2$ in which $R^1$ is as defined above and can be identical or different. $R^2$ can have the same definitions as $R^1$ and additionally can be $C_6$-$C_{12}$ aryl: phenyl, o-, m- or p-tolyl, xylyl or naphthyl, for example. $R^2$ can in each case be identical or different. Examples of organotin catalysts are tin(II) n-octanoate, tin(II) 2-ethylhexanoate, tin(II) laurate, dibutyltin oxide, diphenyltin oxide, dibutyltin dichloride, dibutyltin diacetate, dibutyltin dilaurate, dibutyltin dimaleate or dioctyltin diacetate. Also conceivable are organoantimony, -bismuth or -aluminum catalysts. Particularly preferred representatives of acidic organometallic catalysts are dibutyltin oxide, diphenyltin oxide and dibutyltin dilaurate.

Preferred acidic organic catalysts are acidic organic compounds containing, for example, phosphate groups, sulfonic acid groups, sulfate groups or phosphonic acid groups. Particular preference is given to sulfonic acids such as para-toluenesulfonic acid, for example. Acidic ion exchangers can also be used as acidic organic catalysts, examples being polystyrene resins which contain sulfonic acid groups and have been crosslinked with about 2 mol % of divinylbenzene.

Combinations of two or more of the aforementioned catalysts can also be employed. A further possibility is to use organic or organometallic or else inorganic catalysts that are in the form of discrete molecules in an immobilized form, on silica gel or on zeolites, for example. If it is desired to use acidic inorganic, organometallic or organic catalysts then the amount of catalyst used is in accordance with the invention from 0.001% to 10% by weight, preferably from 0.01% to 1% by weight.

The reaction time is typically from 5 minutes to 48 hours, preferably from 30 minutes to 24 hours and more preferably from 1 hour to 10 hours. The end of the reaction can often be recognized by the fact that the viscosity of the reaction mixture suddenly starts to rise rapidly. When the viscosity rise begins, the reaction can be stopped, for example by cooling. Thereafter, the carboxyl group number in the (pre) polymer can be determined on a sample of the mixture, for example by titration of the acid number to DIN 53402-2.

The reaction of the monomers described typically forms ester bonds. The resulting hyperbranched polyesters are essentially uncrosslinked. In the context of this invention, essentially uncrosslinked means that a degree of crosslinking of less than 15% by weight, preferably of less than 10% by weight, determined via the insoluble content of the polymer, is present. The insoluble content of the polymer was determined by extraction for four hours with the same solvent as is used for the gel permeation chromatography, i.e. tetrahydrofuran, dimethylacetamide or hexafluoroisopropanol, according to the solvent in which the polymer has better solubility, in a Soxhlet apparatus and, after drying the residue to constant weight, weighing the remaining residue.

When working without solvent, the end product is generally obtained directly and, if required, can be purified by customary purifying operations. When a solvent has also been used, it can typically be removed from the reaction mixture after the reaction, for instance by vacuum distillation.

The preparation is notable for its great simplicity. It enables the preparation of hyperbranched polyesters in a simple one-pot reaction. The isolation or purification of intermediates or protecting groups for intermediates is not required. Further details of the preparation of hyperbranched polyesters are given, for example, in WO 01/46296, DE 101 63 163, DE 102 19 508, DE 102 40 817 or WO 99/16810. The hyperbranched polyesters are prepared usually within a pressure range from 2 mbar to 20 bar, preferably at standard pressure, in reactors or reactor cascades which are operated batchwise, semicontinuously or continuously. Through the aforementioned establishment of the reaction conditions and optionally through the selection of the suitable solvent, the inventive products can be processed further without further purification after the preparation.

Preference is given to hyperbranched polyesters which have a weight-average molecular weight in the range from about 500 to 100 000, more preferably of 1000 to 50 000. In the case of a hyperbranched polyester joined to one polyalkylene oxide group, the molecular weight relates only to the part of the hyperbranched polyester without the polyalkylene oxide group. The determination is usually effected by gel permeation chromatography with a refractometer as the detector. Preference is given to performing the determination as described in the examples.

The polydispersity of the polyesters used in accordance with the invention is generally from 1.2 to 50, preferably from 1.4 to 40, more preferably from 1.5 to 30 and most preferably from 2 to 30. The polydispersity data and the number-average and weight-average molecular weight data $M_n$ and $M_w$ are based here on gel permeation chromatography analyses, using polymethyl methacrylate as the standard and tetrahydrofuran, dimethylacetamide or hexafluoroisopropanol as the eluent. The method is described in Analytiker Taschenbuch [Analyst's Handbook], Volume 4, pages 433 to 442, Berlin 1984.

The type of terminal groups can be influenced by the ratio of the monomers used. If predominantly OH-terminated polymers are to be obtained, the alcohols should be used in excess. If predominantly COOH-terminated polymers are to be obtained, the carboxylic acids should be used in excess.

The number of free OH groups (hydroxyl number) of the hyperbranched polyester is generally from 10 to 500 mg, preferably from 20 to 450 mg of KOH per gram of polymer and can be determined, for example, by titration to DIN 53240-2.

The number of free COOH groups (acid number) of the hyperbranched polyester is generally from 0 to 400, preferably from 25 to 300, even more preferably 50 to 250 and especially 120 to 250 mg KOH per gram of polymer and can likewise be determined by titration to DIN 53402.

The hyperbranched polyesters used in accordance with the invention generally have at least 4 functional groups. There is in principle no upper limit in the number of functional groups. However, products having too high a number of functional groups frequently have undesired properties, for example poor solubility or a very high viscosity. The hyperbranched polymers used in accordance with the invention therefore generally have not more than 100 functional groups. The hyperbranched polymers preferably have from 6 to 50 and more preferably from 6 to 30 functional groups.

Nitrogen Containing Hyperbranched Polymers (a3)

Additionally preferred are hyperbranched nitrogen-containing polymers a3 from the group of the polyureas, polyurethanes, polyamides, polyesteramides and polyesteramines, whose structure and preparation are described in WO 2006/087227.

Preferred as nitrogen containing hyperbranched polymers (a3) are hyperbranched polyimides. Structure and synthesis of such compounds are disclosed e.g. in WO 2014/032948. Preferred hyperbranched polyimides are based on pyromellitic dianhydride and diphenylmethane diisocyanate.

Further preferred polymers a3 are hyperbranched polyureas, the term "polyurea" in the context of the polymers a3 comprising not just those polymers whose repeat units are joined to one another by urea groups but quite generally polymers obtainable by reacting at least one di- and/or polyisocyanate with at least one compound which has at least one group reactive toward isocyanate groups. These include polymers whose repeat units, as well as urea groups, are also connected by urethane, allophanate, biuret, carbodiimide, amide, uretonimine, uretdione, isocyanurate or oxazolidone (oxazolidinone) groups (see, for example, Kunststofftaschenbuch [Plastics Handbook], Saechtling, 26th ed., p. 491ff., Carl-Hanser-Verlag, Munich 1995). The term "polyureas" comprises especially polymers which have urea and/or urethane groups.

The hyperbranched polymers a3 used in accordance with the invention preferably have, as well as urea and/or urethane groups (or further groups arising from the reaction of isocyanate groups), at least four further functional groups. The proportion of functional groups is preferably 4 to 100, more preferably 4 to 30 and especially 4 to 20.

Preference is given to polyureas a3 which have a weight-average molecular weight in the range from about 500 to 100 000, preferably 1000 to 50 000.

Their content of urea and/or urethane groups (and, if present, further groups obtained by reaction of an isocyanate group with a group which is reactive toward it and has an active hydrogen atom) is preferably within a range from 0.5 to 10 mol/kg, more preferably 1 to 10 mol/kg, especially 2 to 8 mol/kg.

Useful di- and polyisocyanates include the aliphatic, cycloaliphatic, araliphatic and aromatic di- or polyisocyanates which are known in the prior art and are specified below by way of example. These preferably include 4,4'-diphenylmethane diisocyanate, the mixtures of monomeric diphenylmethane diisocyanates and oligomeric diphenylmethane diisocyanates (polymeric MDI), tetramethylene diisocyanate, tetramethylene diisocyanate trimers, hexamethylene diisocyanate, hexamethylene diisocyanate trimers, isophorone diisocyanate trimer, 4,4'-methylenebis(cyclohexyl) diisocyanate, xylylene diisocyanate, tetramethylxylylene diisocyanate, dodecyl diisocyanate, lysine alkyl ester diisocyanate where alkyl is $C_1$-$C_{10}$-alkyl, 1,4-diisocyanatocyclohexane or 4-isocyanatomethyl-1,8-octamethylene diisocyanate.

Suitable di- or polyisocyanates for forming the polyureas and polyurethanes are more preferably those which have NCO groups of different reactivity. These include 2,4-tolylene diisocyanate (2,4-TDI), 2,4'-diphenylmethane diisocyanate (2,4'-MDI), triisocyanatotoluene, isophorone diisocyanate (IPDI), 2-butyl-2-ethylpentamethylene diisocyanate, 2,2,4- or 2,4,4-trimethyl-1,6-hexamethylene diisocyanate, 2-isocyanatopropylcyclohexyl isocyanate, 3(4)-isocyanatomethyl-1-methylcyclohexyl isocyanate, 1,4-diisocyanato-4-methylpentane, 2,4'-methylenebis(cyclohexyl) diisocyanate and 4-methylcyclohexane 1,3-diisocyanate (H-TDI).

Additionally suitable for forming the polyureas and polyurethanes are isocyanates whose NCO groups at first have equal reactivity, but in which first addition of a reactant onto one NCO group can induce a decline in reactivity in the second NCO group. The examples thereof are isocyanates whose NCO groups are coupled via a delocalized π electron system, for example 1,3- and 1,4-phenylene diisocyanate, 1,5-naphthylene diisocyanate, diphenyl diisocyanate, toluidine diisocyanate or 2,6-tolylene diisocyanate.

In addition, it is possible to use, for example, oligo- or polyisocyanates which can be prepared from the abovementioned di- or polyisocyanates or mixtures thereof by joining by means of urea, allophanate, urethane, biuret, uretdione, amide, isocyanurate, carbodiimide, uretonimine, oxadiazinetrione or iminooxadiazinedione structures.

The compounds having at least two isocyanate-reactive groups used are preferably di-, tri- or tetrafunctional compounds whose functional groups have a different reactivity toward NCO groups.

For the preparation of polyureas, preference is given to using isocyanate-reactive products which have at least two amino groups in the molecule.

These are, for example, ethylenediamine, N-alkylethylenediamine, propylenediamine, N-alkylpropylenediamine, hexamethylenediamine, N-alkylhexamethylenediamine, diaminodicyclohexylmethane, phenylenediamine, isophoronediamine, amine-terminated polyoxyalkylenepolyols (so-called Jeffamines), bis(aminoethyl)amine, bis(aminopropyl)amine, bis(aminohexyl)amine, tris(aminoethyl)amine, tris(aminopropyl)amine, tris(aminohexyl)amine, trisaminohexane, 4-aminomethyl-1,8-octamethylenediamine, N'-(3-aminopropyl)-N,N-dimethyl-1,3-propanediamine, trisaminononane or melamine. In addition, mixtures of the compounds mentioned are also usable.

Preferred compounds for preparing polyurethanes and polyurea-polyurethanes are those having at least one primary and at least one secondary hydroxyl group, at least one hydroxyl group and at least one mercapto group, more preferably having at least one hydroxyl group and at least one amino group, in the molecule, especially aminoalcohols, aminodiols and aminotriols, since the reactivity of the amino group compared to the hydroxyl group in the reaction with isocyanate is significantly higher. Examples of the compounds having at least two isocyanate-reactive groups mentioned are propylene glycol, glycerol, mercaptoethanol, ethanolamine, N-methylethanolamine, diethanolamine, ethanolpropanolamine, dipropanolamine, diisopropanolamine, 2-amino-1,3-propanediol, 2-amino-2-methyl-1,3-propanediol or tris(hydroxymethyl)aminomethane. In addition, mixtures of the compounds mentioned are also usable.

Hyperbranched polyurethanes and polyureas with chain-extended branches can be obtained, for example, by using, for the polymerization reaction, as well as the $AB_x$ molecules, additionally a diisocyanate and a compound which has two groups reactive with isocyanate groups in a molar ratio of 1:1. These additional AA and BB compounds may also possess further functional groups which, however, must not be reactive toward the A or B groups under the reaction conditions. In this manner, further functionalities can be introduced into the hyperbranched polymer.

Linker (b)

The hyperbranched polymer is joined to the polyalkylene oxide chains (c) by means of a linker, preferably polyisocyanate linker. The linker-reactive group used may be a hydroxyl group at the chain end of the polyalkylene oxide chains (c). Polyalkylene oxide chains (c) have exactly one linker-reactive group at the chain end. Suitable polyisocyanate linkers are polyisocyanates with a functionality based on the isocyanate groups of at least 1.5, particularly 1.5 to 4.5 and especially 1.8 to 3.5, comprising aliphatic, cycloaliphatic and aromatic di- and polyisocyanates, and the isocyanurates, allophanates, uretdiones and biurets of aliphatic, cycloaliphatic and aromatic diisocyanates. The polyisocyanates preferably have an average of 1.8 to 3.5 isocyanate groups per molecule. Examples of suitable polyisocyanates are aromatic diisocyanates such as toluene 2,4-diisocyanate, toluene 2,6-diisocyanate, commercially available mixtures of toluene 2,4- and 2,6-diisocyanate (TDI), n-phenylene diisocyanate, 3,3'-diphenyl-4,4'-biphenylene diisocyanate, 4,4'-biphenylene diisocyanate, 4,4'-diphenylmethane diisocyanate, 2,4'-diphenylmethane diisocyanate, 3,3'-dichloro-4,4'-biphenylene diisocyanate, cumene 2,4-diisocyanate, 1,5-naphthalene diisocyanate, p-xylylene diisocyanate, p-phenylene diisocyanate, 4-methoxy-1,3-phenylene diisocyanate, 4-chloro-1,3-phenylene diisocyanate, 4-ethoxy-1,3-phenylene diisocyanate, 2,4-dimethylene-1,3-phenylene diisocyanate, 5,6-dimethyl-1,3-phenylene diisocyanate, 2,4-diisocyanatodiphenyl ether, aliphatic diisocyanates such as ethylene diisocyanate, ethylidene diisocyanate, propylene 1,2-diisocyanate, 1,6-hexamethylene diisocyanate (HDI), 1,4-tetramethylene diisocyanate, 1,10-decamethylene diisocyanate, and cycloaliphatic diisocyanates such as isophorone diisocyanate (IPDI), cyclohexylene 1,2-diisocyanate, cyclohexylene 1,4-diisocyanate and bis(4,4'-isocyanatocyclohexyl)methane. Among the polyisocyanates, preference is given to those whose isocyanate groups differ in terms of reactivity, such as toluene 2,4-diisocyanate, toluene 2,6-diisocyanate, 4'-diphenylmethane diisocyanate, cis- and trans-isophorone diisocyanate, or mixtures of these compounds. Cycloaliphatic diisocyanates, in particular isophorone diisocyanates are preferred.

The reaction with the polyisocyanate linker is effected in the melt or in an organic solvent, preferably in an aprotic polar organic solvent or mixtures of such solvents. Examples are ketones (for example acetone), butyl acetate, tetrahydrofuran (THF), xylene, chlorobenzene, dimethyl sulfoxide (DMSO) or dimethylformamide (DMF). Preferred solvents are butyl acetate, xylene and acetone. The reaction is effected typically at elevated temperatures, the temperature also being guided by the boiling temperature of the solvent selected. The reaction of the polyisocyanate linker with the first component can be effected at 20 to 80° C., but if desired also up to 100° C. The reaction of the further isocyanate group can be effected at temperatures of 50 to 100° C. The solvent can subsequently be removed by distillation.

The reaction can be effected in an equimolar manner, which means that the quantitative ratio is selected such that 1 mol of diisocyanate is used per mole of hydroxyl groups of the functionalizing reagent or of the linear polyalkylene oxide to be converted. Preference is given to working with a slight (e.g. 0 to 15 mol %) excess of the hydroxyl groups, in order to reduce the amount of unconverted diisocyanate. In the case of symmetric diisocyanates (such as HDI), it may also be advisable to use an excess of diisocyanate and to remove the excess subsequently by distillation.

Preference is given to performing the reaction in the presence of a catalyst. Suitable catalysts are, for example, tertiary amines, for example triethylamine, tri-n-propylamine, N-methylpyrrolidine, N-methylpiperidine and diazabicyclooctane (DABCO), zinc carboxylates, bismuth carboxylates, titanium alkoxides, organotin compounds, especially dialkyltin(IV) salts of aliphatic carboxylic acids such as dibutyltin dilaurate and dibutyltin dioctoate, tin(II) dialkoxides such as tin dioctoate, and cesium salts such as cesium acetate. In one embodiment, tin carboxylates, bismuth carboxylates, titanium alkoxides are particular suitable, the carboxylates preferably being $C_1$-$C_{20}$ carboxylates (such as formate, acetate, propionate, hexanoate, octanoate or neodecanoate). The catalyst can be used in amounts of 50 to 50 000 ppm, preferably 100 to 5000 ppm, based on all of the solids.

Typically, the reaction will be performed in such a way that the component which is to be functionalized with isocyanate groups (for example the polar polymer) is first reacted with the diisocyanate in the presence of the catalyst and of a solvent until the isocyanate value in the reaction mixture has fallen by half. When a slight hydroxyl group excess is used, conversion is continued until the theoretical end value corresponds to the complete conversion of the hydroxyl groups. This can be determined in a known manner, for example by titrimetric means. This is then followed by the addition of the hyperbranched polyester. The molar ratio of hyperbranched polyester to the polyalkylene oxide or to the functional $C_1$-$C_{24}$ end group comprising one acid group or two alcohol groups is 1:1 to 1:25, preferably 1:2 to 1:15. The reaction is continued until the isocyanate value has fallen to zero.

Polyalkylene Oxide Shell (c)

The polyalkylene oxide shell (c) comprises (preferably consists of)
c1) one or more polyethylene glycol monomethyl ethers and
c2) one or more poly($C_2$-$C_3$)alkylene glycol mono-($C_8$-$C_{22}$)-alkyl ethers,
wherein the weight ratio of components c1):c2) is from 9:1 to 1:9.

The polyethylene glycol monomethyl ether (c1) (MPEGs) generally has a molecular weight of 300 to 2000 g/mol, preferably 750 to 1000 g/mol, as determined by GPC. The average number of repeating units p of the ethylen glyol group is generally from 5 to 50, preferably from 15 to 25.

Suitable examples of polyethylene glycol monomethyl ether (c1) are compounds of the formula

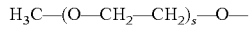

$$H_3C-(O-CH_2-CH_2)_s-O-$$

wherein s is a natural number from 1 to 50, preferably from 5 to 50, more preferably from 15 to 25. The open bond at the oxygen atom is the typical position where the molecule is bound to the linking group b).

Suitable MPEGs are known and are commercially available, e.g., as Pluriol® A 350 E, Pluriol® A 750 E and Pluriol® A 1020 from BASF SE, or Carbowax® 350 and 750 from Dow Chemicals.

The polyalkylene glycol monoalkyl ethers (c2) are compounds of the formula

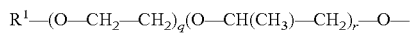

$$R^1-(O-CH_2-CH_2)_q(O-CH(CH_3)-CH_2)_r-O-$$

wherein
each $R^1$ is independently linear or branched $C_8$-$C_{22}$-alkyl;
q is a natural number from 1 to 50; and
r is 0 or is a natural number from 1 to 30, with the proviso that 5 q+r 50.

The open bond at the oxygen atom is the typical position where the molecule is bound to the linking group b).

The compound (c2) generally has a molecular weight of from 300 to 2000. Suitable alkyl polyalkylene glykols (FAPEGs) are known and commercially available, e.g., as Lutensol® AT 11, Lutensol® AT 25, Lutensol® A7N, Plurafac® LF 1300, LF 700 and LF 1304 from BASF SE or Genapol® T200-800 and Genapol® LA070, 160 from Clariant.

As the fatty alcohols $R^1$—OH often derive from natural sources it is common to have mixtures, e.g. of $C_{16}$ and $C_{18}$ alcohols or $C_{12}$ and $C_{14}$ alcohols.

The weight ratio (c1):(c2) is in the range of from 9:1 to 1:9, preferably 7:3 to 1:9, more preferably 7:3 to 2:8, even more preferably 5:1 to 1:3, and even more preferred 3:1 to 1:1.5.

In a preferred form the weight ratio (c1):(c2) is in the range of from 85:15 to 15:85, preferably 8:2 to 2:8, more preferred 7:3 to 3:7.

In another form suitable examples of the weight ratio (c1):(c2) are ranges such as
from 9:1 to 1:9,
from 7:3 to 1:9,
from 7:3 to 2:8,
from 5:1 to 1:3,
from 3:1 to 1:1.5,
from 85:15 to 15:85,
from 8:2 to 2:8, or
from 7:3 to 3:7.

The molar ratio of (c1) to (c2) in mol-% is generally in the range of from 95%:5% to 5%:95%, preferably 80%:20% to 25%:75%, more preferred 75%:25% to 40%:60%.

In general 70 to 100% of the groups (c1) and (c2) carry an end group $R^1$ or methyl, preferably at least 95%.

The invention further relates to a composition comprising the hyperbranched polymer of the invention and an active ingredient, preferably a sparingly water-soluble active ingredient, in particular a pesticidal or pharmaceutical active ingredient.

"Active ingredient" as used herein means a physiologically active substance from the field of pesticides, pharmaceuticals, nutrition and cosmetics.

The composition comprises one or more different active ingredients. Examples of active ingredients are active pesticidal ingredients, active cosmetic ingredients, active pharmaceutical ingredients or food supplements (such as vitamins or carotenoids). Preferred active ingredients are pesticidal active ingredients and pharmaceutical active ingredients, in particular pesticidal active ingredients.

The active ingredient is preferably sparingly water soluble.

According to the invention, the maximum solubility of a sparingly-water soluble active ingredient in water at 20° C. is 10 g/l, preferably 2 g/l, more preferably 0.5 g/l and especially 0.1 g/l.

Examples of pesticidal active ingredients are listed below.

Examples of active pharmaceutical ingredients include: benzodiazepines, antihypertensives, vitamins, cytostatics, especially taxol, anesthetics, neuroleptics, antidepressives, antiviral agents, for example anti-HIV agents, antibiotics, antimycotics, antidementia drugs, fungicides, chemotherapeutics, urologics, platelet aggregation inhibitors, sulfonamides, spasmolytics, hormones, immunoglobulins, sera, thyroid therapeutics, psychoactive drugs, Parkinson's drugs and other antihyperkinetics, ophthalmics, neuropathy preparations, calcium metabolism regulators, muscle relaxants, anesthetics, lipid-lowering drugs, hepatotherapeutics, coronary drugs, cardiac drugs, immunotherapeutics, regulatory peptides and inhibitors thereof, hypnotics, sedatives, gynecologicals, gout remedies, fibrinolytics, enzyme preparations and transport proteins, enzyme inhibitors, emetics, blood flow stimulators, diuretics, diagnostic agents, corticoids, cholinergics, biliary therapeutics, antiasthmatics, bronchodilators, beta receptor blockers, calcium antagonists, ACE inhibitors, arteriosclerosis drugs, antiinflammatories, anticoagulants, antihypotensives, antihypoglycemics, antihypertensives, antifibrinolytics, antiepileptics, antiemetics, antidotes, antidiabetics, antiarrhythmics, antianemics, antiallergics, anthelmintics, analgesics, analeptics, aldosterone antagonists, slimming agents.

Examples of active cosmetic ingredients are cosmetic oils, flavorings and aromas, vitamins or UV absorbers. Cosmetic oils include peanut oil, jojoba oil, coconut oil, almond oil, olive oil, palm oil, castor oil, soybean oil, wheatgerm oil, or essential oils such as mountain pine oil, lavender oil, rosemary oil, spruce needle oil, pine needle oil, eucalyptus oil, peppermint oil, sage oil, bergamot oil, turpentine oil, melissa oil, juniper oil, lemon oil, anise oil, cardamom oil, camphor oil, etc., or mixtures thereof. UV absorbers include 2-hydroxy-4-methoxybenzophenone, 2,2', 4,4'-tetrahydroxybenzophenone, 2,2'-dihydroxy-4,4'-dimethoxybenzophenone, 2,4-dihydroxybenzophenone, 2'-ethylhexyl 2-cyano-3,3-diphenylacrylate, 2,4,6-trianilino-p-(carbo-2'-ethylhexyl-1'-oxy)-1,3,5-triazine, 3-(4-methoxybenzylidene)camphor, 2-ethylhexyl N,N-dimethyl-4-aminobenzoate, 3,3,5-trimethylcyclohexyl salicylate, 4-isopropyldibenzoylmethane, 2-ethylhexyl p-methoxycinnamate and 2-isoamyl p-methoxycinnamate, and mixtures thereof.

Examples of flavorings and aromas are as described, e.g., in WO 01/49817, or in "Flavors and Fragrances", Ullmann's Encyclopedia of Industrial Chemistry, Wiley-VCH, 2002, to which explicit reference is made.

Examples of vitamins are vitamins, provitamins and vitamin precursors from groups A, C, E and F, especially 3,4-didehydroretinol, beta-carotene (provitamin of vitamin A), ascorbic acid (vitamin C), and the palmitic esters, glucosides or phosphates of ascorbic acid, tocopherols, especially alpha-tocopherol and esters thereof, for example the acetate, the nicotinate, the phosphate and the succinate; and additionally vitamin F, which is understood to mean essential fatty acids, particularly linolic acid, linolenic acid and arachidonic acid.

The active ingredient is more preferably a pesticidal active ingredient, preferably a sparingly-water soluble pesticidal active ingredient.

The term "pesticidal active ingredients" (also referred to hereinafter as pesticides) refers to at least one active ingredient selected from the group of fungicides, insecticides, nematicides, herbicides, safeners and/or growth regulators. The term "insecticide" as used herein encompasses compounds with insecticidal and/or accaricidal activity. Preferred pesticides are fungicides, insecticides and herbicides, especially fungicides. Mixtures of pesticides from two or more of the abovementioned classes can also be used. The person skilled in the art is familiar with such pesticides, which can be found, for example, in The Pesticide Manual, 16th Ed. (2012), The British Crop Protection Council, London. Suitable fungicides are, e.g., fungicides of the classes dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzylcarbamates, carbamates, carboxamides, carboxylic acid amides, chloronitriles, cyanoacetamide oximes, cyanoimidazoles, cyclopropanecarboxamides, dicarboximides, dihydrodioxazines, dinitrophenylcrotonates, dithiocarbamates, dithiolanes, ethylphosphonates, ethylaminothiazolecarboxamides, guanidines, hydroxy-(2-amino)pyrimidines, hydroxyanilides, imidazoles, imidazolinones, inorganic compounds, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable insecticides are, e.g., insecticides from the class of carbamates, organophosphates, organochlorine insecticides, phenylpyrazoles, pyrethroids, neonicotinoids, spinosins, avermectins, milbemycins, juvenile hormone analogs, alkyl halides, organotin compounds, nereistoxin analogs, benzoylureas, diacylhydrazines, METI acaricides, and insecticides such as chloropicrin, pymetrozine, flonicamid, clofentezine, hexythiazox, etoxazole, diafenthiuron, propargite, tetradifon, chlorfenapyr, DNOC, buprofezin, cyromazine, amitraz, hydramethylnon, acequinocyl, fluacrypyrim, rotenone, or derivatives thereof.

Suitable herbicides are, e.g., herbicides of the classes of acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ethers, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

In one embodiment, the pesticide comprises a fungicide; the pesticide preferably consists of at least one fungicide. Examples of fungicides are fluxapyroxad, pyraclostrobin, metconazol and epoxiconazol.

In a further embodiment, the pesticide comprises an insecticide; the pesticide more preferably consists of at least one insecticide. Preferred insecticides are fipronil, allethrin, alpha-cypermethrin, beta-cyfluthrin, bifenthrin, bioallethrin, 4-chloro-2-(2-chloro-2-methylpropyl)-5-[(6-iodo-3-pyridinyl)methoxy]-3(2H)pyridazinone (CAS RN:120955-77-3), chlorfenapyr, chlorpyrifos, cyfluthrin, cyhalothrin, cypermethrin, deltamethrin, etofenprox, fenoxycarb, flufenoxuron, hydramethylnon, metaflumizone, permethrin, pyriproxifen, silafluofen, tebufenozide and tralomethrin. Particularly preferred insecticides are fipronil, alpha-cypermethrin, bifenthrin, chlorfenapyr, cyfluthrin, cypermethrin, deltamethrin, etofenprox, hydramethylnon, metaflumizone, permethrin. Very particularly preferred insecticides are fipronil, alpha-cypermethrin, deltamethrin, chlorfenapyr, hydramethylnon and metaflumizone. An especially preferred insecticide is fipronil.

In a further embodiment, the pesticide comprises a herbicide; the pesticide preferably consists of at least one herbicide. In a further embodiment, the pesticide comprises a growth regulator; the pesticide preferably consists of at least one growth regulator.

The composition typically comprises 0.5 to 50% by weight of active ingredient, preferably 1 to 30% by weight, especially 5 to 20% by weight, based on the composition. The composition usually comprises 3 to 50% by weight, preferably 5 to 30% by weight, more preferably 10 to 20% by weight, of dendron (I).

The weight ratio of the hyperbranched polymer of the invention to active ingredient is usually in the range from 1:50 to 100:1, preferably 1:5 to 50:1, more preferably 1:2 to 25:1. The active ingredient may be present in dissolved form or in solid particulate form. The active ingredient particles may be crystalline or amorphous. The particle size may be 1 nm to 10 μm.

The invention preferably relates to agrochemical compositions comprising the inventive mixture of the hyperbranched polymer of the invention and a pesticide.

Examples for composition types of the agrochemical composition are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

The agrochemical compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are preferably water but include organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-subsituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-subsitiued fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B—C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable negligible or even no pesticidal activity themselves, and which improve the biological performance of the compound I on the target. Examples are surfactants, mineral or vegetable oils, and other auxiliaries. Further exampies are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes.

Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:

i) Water-soluble concentrates (SL, LS)

10-60 wt-% of a mixture according to the invention and 5-15 wt-% wetting agent (e.g. alcohol alkoxylates) are dissolved in water and/or in a water-soluble solvent (e.g. alcohols) up to 100 wt-%. The active substance dissolves upon dilution with water.

ii) Dispersible concentrates (DC)

5-25 wt-% of a mixture according to the invention and 1-10 wt-% dispersant (e. g. polyvinylpyrrolidone) are dissolved in up to 100 wt-% organic solvent (e.g. cyclohexanone). Dilution with water gives a dispersion.

iii) Emulsifiable concentrates (EC)

15-70 wt-% of a mixture according to the invention and 5-10 wt-% emulsifiers (e.g. calcium dodecylbenzenesulfonate and castor oil ethoxylate) are dissolved in up to 100 wt-% water-insoluble organic solvent (e.g. aromatic hydrocarbon). Dilution with water gives an emulsion.

iv) Emulsions (EW, EO, ES)

5-40 wt-% of a mixture according to the invention and 1-10 wt-% emulsifiers (e.g. calcium dodecylbenzenesulfonate and castor oil ethoxylate) are dissolved in 20-40 wt-% water-insoluble organic solvent (e.g. aromatic hydrocarbon). This mixture is introduced into up to 100 wt-% water by means of an emulsifying machine and made into a homogeneous emulsion. Dilution with water gives an emulsion.

v) Suspensions (SC, OD, FS)

In an agitated ball mill, 20-60 wt-% of a mixture according to the invention are comminuted with addition of 2-10 wt-% dispersants and wetting agents (e.g. sodium lignosulfonate and alcohol ethoxylate), 0.1-2 wt-% thickener (e.g. xanthan gum) and up to 100 wt-% water to give a fine active substance suspension. Dilution with water gives a stable suspension of the active substance. For FS type composition up to 40 wt-% binder (e.g. polyvinylalcohol) is added.

vi) Water-dispersible granules and water-soluble granules (WG, SG)

50-80 wt-% of a mixture according to the invention are ground finely with addition of up to 100 wt-% dispersants and wetting agents (e.g. sodium lignosulfonate and alcohol ethoxylate) and prepared as water-dispersible or water-soluble granules by means of technical appliances (e. g. extrusion, spray tower, fluidized bed). Dilution with water gives a stable dispersion or solution of the active substance.

vii) Water-dispersible powders and water-soluble powders (WP, SP, WS)

50-80 wt-% of a mixture according to the invention are ground in a rotorstator mill with addition of 1-5 wt-% dispersants (e.g. sodium lignosulfonate), 1-3 wt-% wetting agents (e.g. alcohol ethoxylate) and up to 100 wt-% solid carrier, e.g. silica gel. Dilution with water gives a stable dispersion or solution of the active substance.

viii) Gel (GW, GF)

In an agitated ball mill, 5-25 wt-% of a mixture according to the invention are comminuted with addition of 3-10 wt-% dispersants (e.g. sodium lignosulfonate), 1-5 wt-% thickener (e.g. carboxymethylcellulose) and up to 100 wt-% water to give a fine suspension of the active substance. Dilution with water gives a stable suspension of the active substance.

iv) Microemulsion (ME)

5-20 wt-% of a mixture according to the invention are added to 5-30 wt-% organic solvent blend (e.g. fatty acid dimethylamide and cyclohexanone), 10-25 wt-% surfactant blend (e.g. alcohol ethoxylate and arylphenol ethoxylate), and water up to 100%. This mixture is stirred for 1 h to produce spontaneously a thermodynamically stable microemulsion.

iv) Microcapsules (CS)

An oil phase comprising 5-50 wt-% of a mixture according to the invention, 0-40 wt-% water insoluble organic solvent (e.g. aromatic hydrocarbon), 2-15 wt-% acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt-% of a mixture according to the invention, 0-40 wt-% water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt-%. The wt-% relate to the total CS composition.

ix) Dustable powders (DP, DS)

1-10 wt-% of a mixture according to the invention are ground finely and mixed intimately with up to 100 wt-% solid carrier, e.g. finely divided kaolin.

x) Granules (GR, FG)

0.5-30 wt-% of a mixture according to the invention is ground finely and associated with up to 100 wt-% solid carrier (e.g. silicate). Granulation is achieved by extrusion, spray-drying or the fluidized bed.

xi) Ultra-low volume liquids (UL)

1-50 wt-% of a mixture according to the invention are dissolved in up to 100 wt-% organic solvent, e.g. aromatic hydrocarbon.

The compositions types i) to xi) may optionally comprise further auxiliaries, such as 0.1-1 wt-% bactericides, 5-15 wt-% anti-freezing agents, 0.1-1 wt-% anti-foaming agents, and 0.1-1 wt-% colorants.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100% (according to NMR spectrum).

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and other pesticides (e.g. herbicides, insecticides, fungicides, growth regulators, safeners) may be added to the active substances or the agrochemical compositions comprising them as premix or, if appropriate not until immediately prior to use (tank mix). These agents can be admixed with the agrochemical compositions according to the invention in a weight ratio of 1:100 to 100:1, preferably 1:10 to 10:1.

The user applies the agrochemical composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

The invention further relates to a process for producing the inventive composition by contacting the hyperbranched polymer of the invention and the active ingredient. The components can be contacted by commonly known methods, such as mixing, emulsifying or suspending.

The invention further relates to the use of the hyperbranched polymer of the invention in an agrochemical formulation, comprising the dendron and a pesticide, for controlling phytopathogenic fungi and/or unwanted vegetation and/or unwanted insect or mite infestation and/or for regulating the growth of plants, by allowing the composition to act on the particular pests, their surroundings or the plants to be protected from the particular pests, the soil and/or unwanted plants and/or the crop plants and/or the surroundings thereof. In addition, it is possible to use the inventive composition, especially the agrochemical formulation, to control unwanted insect or mite infestation on plants and/or to control phytopathogenic fungi and/or to control unwanted plant growth, by treating seeds of crop plants with the composition.

The invention further relates to the use of the hyperbranched polymer of the invention for solubilizing a sparingly water-soluble active ingredient in aqueous solutions. The active ingredient preferably has a maximum solubility in water at 20° C. of 10 g/l. "Solubilization" means that more active ingredient can be brought into solution in the presence of the inventive amphiphile than in the absence thereof under otherwise identical conditions. It is preferably possible to bring at least twice the amount, more preferably at least five times the amount and especially ten times the amount into solution.

The invention further relates to a plant propagation material, specifically seeds, comprising the hyperbranched polymer of the invention.

The examples which follow are intended to illustrate the invention without restricting it.

EXAMPLES

All percentages are weight-% if not otherwise indicated. The OH numbers were measured to DIN 53 240. The acid numbers were measured to DIN EN ISO 2114. GPC was carried out with polymethyl methacrylate as standard.
MPEG1: Methyl polyethylene glycol, mean molar mass of 750 g/mol, OH number 80 mg KOH/g.
MPEG2: Methyl polyethyleneglycol, mean molar mass of 1000 g/mol, OH number 50 mg KOH/g.
FAPAG1: Ethoxylated and propoxylated $C_{16}$-$C_{18}$-fatty alcohol, liquid, surface tension about 33 mN/m (1 g/l at 23° C.), viscosity about 128 mPas (Brookfield at 23° C.).
FAPAG2: $C_{16}$-$C_{18}$-fatty alcohol, ethoxylated (about 5 EO) and propoxylated (about 8 PO).
FAPAG3: linear $C_{16}$-$C_{18}$-fatty alcohol polyethylene glycol, degree of ethoxylation about 25, OH number 40 mg KOH/g.
FAPAG4: Linear $C_{16}$-$C_{18}$-fatty alcohol polyethylene glycol, OH number 75 mg KOH/g.
FAPAG5: $C_{16}$-$C_{18}$-Fatty alcohol polyalkylene glycol is commercially available as Plurafac® LF1304 from BASF SE.
FAPAG6: Linear $C_{12}$-$C_{14}$-fatty alcohol polyethylene glycol, OH number about 110 mg KOH/g.
FAPAG7: $C_8$-$C_{10}$ saturated fatty alcohol polyethylene glykol, degree of ethoxylation about 11, OH number about 85 mg KOH/g.
FAPAG8: Isotridecyl alcohol polyalkylene glycol, surface tension about 30 mN/m (1 g/l at 23° C.), viscosity about 75 mPas (Brookfield at 23° C.).
TMP-PO1: branched polyether polyol based on trimethylolpropane and propylene oxide; OH number of 860 mg KOH/g.
TMP-PO2: branched polyether polyol based on trimethylolpropane and propylene oxide; OH number of 160 mg KOH/g
DEC: Diethylcarbonate
poly-THF: Poly-tetrahydrofurane, molecular weight of 1000 g/mol.
Catalyst A: Zinc neodecanoat Synthesis Example 1

Polymer P1 (Hyperbranched Polycarbonate Based on DEC and TMP-PO1 Modified with IPDI, and MPEG1/FAPAG1 in a Weight Ratio of 1.53:1)
1.1 Synthesis of Hyperbranched Polycarbonate PC1

In a four-necked flask equipped with stirrer, reflux condenser, Dean Stark apparatus and internal thermometer 799 g polyfunctional alcohol (TMP-PO1) was mixed with 401 g diethyl carbonate, and 250 ppm catalyst ($K_2CO_3$, based on the polyfunctional alcohol, 120 mg) were added. The mixture was then heated with stirring to 140° C., and stirred for 2 h at this temperature. Ethanol was removed by distillation, and the conversion was determined based on the amount of ethanol formed (250 g, corresponding to 80% conversion). The reaction product was cooled to 90° C., and phosphoric acid was added for neutralization.

TMP-PO1: diethylcarbonate (1:1,1); Mn: 934 g/mol, Mw: 1224 g/mol, OH-number: 454 mg KOH/g
1.2 Modification of the Hyperbranched Polycarbonate PC1 with IPDI, and MPEG1/FAPAG1 in a Weight Ratio of 1.53:1

Step 1: MPEG1 (98.1 g) was melted up and mixed with FAPAG1 (64.2 g) under nitrogen. The two components were homogenized at 50° C. The heat source was removed and IPDI (37.7 g) was added. The NCO content at the start was determined and the reaction mixture was heated to 45° C. The reaction was continued until the desired NCO content was reached.

Step 2: The product obtained in step 1 (181.6 g) was charged with the hyperbranched polycarbonate PC1 (18.4 g), and the NCO content was determined. Catalyst A (200 mg) was added, and the mixture was heated to 80° C. The reaction was continued to an NCO content of 0.0% (100% functionalization).

Content of Polymer P1: 9% hyperbranched polycarbonate PC1, 17% linker, 45% MPEG1, 29% FAPAG1.

Synthesis Example 2

Polymer P2 (Hyperbranched Polyester Based on Trimethylolpropane (TMP) and Sebacinic Acid Diethyl Ester Modified with IPDI, and MPEG1/FAPAG1 in a Weight Ratio of 1.53:1)
2.1 Synthesis of Hyperbranched Polyester PE1

In a four-necked flask equipped with stirrer, reflux condenser, Dean Stark apparatus and internal thermometer TMP (341.8 g) was mixed with sebacinic acid diethyl ester (658.2 g, molar ratio with TMP 1:1) and KOH (10% in ethanol, 10.0 g) were added. The mixture was melted up at 80° C., and then heated with stirring to 140° C. Ethanol was removed by distillation, and complete conversion was determined based on the amount of ethanol formed (148 g). The reaction product was cooled to 60° C., and the pH value was adjusted to 6 by adding phosphoric acid.
2.2 Modification of the Hyperbranched Polyester PE1 with IPDI and MPEG1/FAPAG1 in a Weight Ratio of 1.53:1

Step 1: MPEG1 (115.3 g) was melted up at 60° C. in a drying oven, and mixed with FAPAG1 (75.4 g) under nitrogen. The two components were homogenized at 50° C. The heat source was removed and IPDI (44.3 g) was added. The NCO content at the start was determined and the reaction mixture was heated to 45° C. The reaction was continued until the desired NCO content was reached.

Step 2: The product obtained in step 1 (75.5 g) was charged with the hyperbranched polyester PE1 (125.4 g), and the NCO content was determined. Catalyst A (200 mg) was added, and the mixture was heated to 80° C. The reaction was continued to an NCO content of 0.0% (100% functionalization).

Content of Polymer P2: 63% hyperbranched polyester PE1, 7% linker, 18% MPEG1, 12% FAPAG1.

Synthesis Example 3

Polymer P3 (Hyperbranched Polyester Based on Poly-THF and Citric Acid Mono Hydrate Modified with IPDI, and MPEG1/FAPAG1 in a Weight Ratio of 1.53:1)
3.1 Synthesis of Hyperbranched Polyester PE2

In a four-necked flask equipped with stirrer, reflux condenser, Dean Stark apparatus and internal thermometer citric acid mono hydrate (77.5 g) was mixed with poly-THF (922.5 g, molar ratio with citric acid mono hydrate 2.5:1). The mixture was melted up at 80° C., and then titanium(IV) butylate (200 mg) was added. Vacuum was applied, and the mixture was heated to 140° C. Water was removed by distillation, and complete conversion was determined based on the amount of water formed, or by determination of the desired acid number.
3.2 Modification of the Hyperbranched Polyester PE2 with IPDI, and MPEG1/FAPAG1 in a Weight Ratio of 1.53:1

Step 1: MPEG1 (142.3 g) was melted up at 60° C. in a drying oven, and mixed with FAPAG1 (93.1 g) under nitrogen. The two components were homogenized at 50° C. The heat source was removed and IPDI (54.7 g) was added. The NCO content at the start was determined and the reaction mixture was heated to 45° C. The reaction was continued until the desired NCO content was reached.

Step 2: The product obtained in step 1 (127.2 g) was charged with the hyperbranched polyester PE2 (72.76 g), and the NCO content was determined. Catalyst A (200 mg) was added, and the mixture was heated to 80° C. The reaction was continued to an NCO content of 0.0% (100% functionalization).

Content of Polymer P3: 63% hyperbranched polyester PE2, 7% linker, 18% MPEG1, 12% FAPEG.

Synthesis Example 4

Polymer P4 (hyperbranched polycarbonate based on DEC and TMP-PO2 modified with IPDI, and MPEG1/FAPAG1 in a weight ratio of 1.53:1)
4.1 Synthesis of Hyperbranched Polycarbonate PC2

In a four-necked flask equipped with stirrer, reflux condenser, Dean Stark apparatus and internal thermometer polyfunctional alcohol (TMP-PO2) was mixed with diethyl carbonate (molar ratio 1:1), and 250 ppm catalyst ($K_2CO_3$, based on the polyfunctional alcohol,) were added. The mixture was then heated with stirring to 140° C., and stirred for 2 h at this temperature. Ethanol was removed by distillation, and the conversion was determined based on the amount of ethanol formed.

TMP-PO2: diethylcarbonate (1:1); Mn: 2500 g/mol, Mw: 4700 g/mol, OH-number: 90 mg KOH/g
4.2 Modification of the Hyperbranched Polycarbonate PC2 with IPDI, and MPEG1/FAPAG1 in a Weight Ratio of 1.53:1

Step 1: MPEG1 (73.6 g) was melted up and mixed with FAPAG1 (48.1 g) under nitrogen. The two components were homogenized at 50° C. The heat source was removed and IPDI (28.3 g) was added. The NCO content at the start was determined and the reaction mixture was heated to 45° C. The reaction was continued until the desired NCO content was reached.

Step 2: The product obtained in step 1 (130.2 g) was charged with the hyperbranched polycarbonate PC2 (69.8 g), and the NCO content was determined. Catalyst A (200 mg) was added, and the mixture was heated to 80° C. The reaction was continued to an NCO content of 0.0% (100% functionalization).

Content of Polymer P4: 35% hyperbranched polycarbonate PC2, 12% linker, 32% MPEG1, 21% FAPAG1.

Synthesis Example 5

Polymer P5 (hyperbranched polyester based on poly-THF and citric acid mono hydrate modified with IPDI, and MPEG1/FAPAG1/FAPAG2 in a weight ratio of 2.21:1.27:1)
5.1 Synthesis of hyperbranched polyester PE2

The synthesis of PE2 was carried out as in synthesis example 3.1
5.2 Modification of the Hyperbranched Polyester PE2 with IPDI, and MPEG1/FAPAG1/FAPAG2 in a Weight Ratio of 2.21:1.27:1

Step 1: MPEG1 (144.1 g) was melted up at 60° C. in a drying oven, and mixed with FAPAG1 (82.5 g) and FAPAG2 (66.2 g) under nitrogen. The components were homogenized at 50° C. The heat source was removed and IPDI (58.2 g) was added. The NCO content at the start was determined and the reaction mixture was heated to 45° C. The reaction was continued until the desired NCO content was reached.

Step 2: The product obtained in step 1 (143.1 g) was charged with the hyperbranched polyester PE2 (56.9 g), and the NCO content was determined. Catalyst A (200 mg) was added, and the mixture was heated to 80° C. The reaction was continued to an NCO content of 0.0% (100% functionalization).

Content of Polymer P5:28% hyperbranched polyester PE2, 12% linker, 29% MPEG1, 17% FAPAG1, 12% FAPAG2.

Synthesis Example 6

Polymer P6 (Hyperbranched Polyimide Based on Pyromellitic Anhydride, 4,4'-Diphenylmethane Diisocyanate, Polypropyleneglycol Modified with IPDI and MPEG1 and FAPAG1 in a Weight Ratio of 1:1:53)
6.1 General Remarks:
Polyisocyanate ($\alpha$.3): 4,4'-diphenylmethane diisocyanate, average of 2 isocyanate groups per molecule, dynamic viscosity: 5 mPa·s at 25° C., commercially available as Lupranat® MES.
Polycarboxylic acid ($\beta$.1): dianhydride of 1,2,4,5-benzene tetracarboxylic acid
Diol (b.2): polypropylenglycol having an average molecular weight Mn of 1100 g/mol
"NCO": NCO content, determined by IR spectroscopy unless expressly mentioned otherwise, it is indicated in % by weight.
The molecular weights were determined by gel permeation chromatography (GPC using a refractometer as detector). The standard used was polymethyl methacrylate (PMMA). The solvents used were N,N-dimethylacetamide (DMAc) or tetrahydrofurane (THF), if not stated otherwise.
Percentages are % by weight unless expressly mentioned otherwise.
The molecular weights were determined by gel-permeation chromatography (GPC). The standard used was polystyrene (PS). The solvent used was tetrahydrofuran (THF), where not explicitly stated otherwise. Detection was performed using an Agilent 1100 differential refractometer or an Agilent 1100 VWD UV photometer.
The NCO content was determined titrimetrically as specified in DIN EN ISO 11 909 and reported in % by weight.
The syntheses were carried out under nitrogen, if not described otherwise.
6.2 Synthesis of Hyperbranched Polyimide PI1
An amount of 100 g (0.46 mol) of polycarboxylic acid ($\beta$.1) were dissolved in 1400 ml of acetone which was not dried before the reaction and therefore comprised water and placed in a 4-l four-neck flask having a dropping funnel, reflux cooler, internal thermometer and Teflon agitator. Then, 173 g (0.69 mol) of polyisocyanate ($\alpha$.3) were added slowly at 20° C. The mixture was heated with stirring to 55° C. The mixture was stirred for a further six hours under reflux at 55° C. and 17 hours at room temperature. Thereafter a mixture of 1100 g of diol (b.2) (1.00 mol) was added at room temperature. The temperature was increased to 55° C. and stirred for six hours.
Then acetone was distilled off at atmospheric pressure in the course of six hours. Thereafter the pressure was decreased to 200 mbar. This produced reaction produced PI1 as a solid red mass.
Mn=4160 g/mol, Mw=8780 g/mol
Mw/Mn=2,1
OH number: 32 mg KOH/g
Acid value: 48 mg KOH/g
6.3 Modification of the Hyperbranched Polyimide PI1 with IPDI and MPEG1/FAPAG1 in a Weight Ratio of 1:1.53
Step 1: MPEG1 93 g, FAPAG1 142 g, IPDI 55 g Step 2: Using PI1 72 g and the reaction mixture from step 1 (135 g) the polymer was synthesized according to the general procedure.

Synthesis Example 7

Polymer 7 (Hyperbranched Polycarbonate Based on DEC and TMP-PO1 Modified with IPDI, and MPEG1/FAPAG2 in a Weight Ratio of 1.93:1)
7.1 Synthesis of Hyperbranched Polycarbonate PC1
The synthesis of PC1 was carried out as in synthesis example 1.1
7.2 Modification of the Hyperbranched Polycarbonate PC1 with IPDI and MPEG1/FAPAG2 in a Weight Ratio of 1.93:1
Step 1: MPEG1 105.18 g, FAPAG2 54.39 g, IPDI 40.43 g
Step 2: PC1 19.61 g, product obtained in step 1:180.39 g.

Synthesis Example 8

Polymer P8 (Hyperbranched Polyester Based on Poly-THF and Citric Acid Mono Hydrate Modified with IPDI, and MPEG1/FAPAG3 in a Weight Ratio of 1.29:1)
8.1 Synthesis of Hyperbranched Polyester PE2
The synthesis of PE2 was carried out as in synthesis example 3.1
8.2 Modification of the Hyperbranched Polyester PE2 with IPDI, and MPEG1/FAPAG3 in a Weight Ratio of 1.29:1
Step 1: MPEG1 138.79 g, FAPAG3 107.86 g, IPDI 53.35 g
Step 2: PE2 70.08 g, product obtained in step 1:129.92 g.

Synthesis Example 9

Polymer P9 (Hyperbranched Polyester Based on Poly-THF and Citric Acid Mono Hydrate Modified with IPDI, and MPEG1/FAPAG4 in a Weight Ratio of 2.36:1)
9.1 Synthesis of Hyperbranched Polyester PE2
The synthesis of PE2 was carried out as in synthesis example 3.1
9.2 Modification of the Hyperbranched Polyester PE2 with IPDI, and MPEG1/FAPAG4 in a Weight Ratio of 2.36:1
Step 1: MPEG1 154.93 g, FAPAG3 65.51 g, IPDI 59.56 g
Step 2: PE2 78.43 g, product obtained in step 1:121.57 g.

Synthesis Example 10

Polymer P10 (Hyperbranched Polyester Based on Poly-THF and Citric Acid Mono Hydrate Modified with IPDI, and MPEG1/FAPAG8 in a Weight Ratio of 2.60:1)
10.1 Synthesis of Hyperbranched Polyester PE2
The synthesis of PE2 was carried out as in synthesis example 3.1
10.2 Modification of the Hyperbranched Polyester PE2 with IPDI, and MPEG1/FAPAG8 in a Weight Ratio of 2.60:1
Step 1: MPEG1 172.37 g, FAPAG8 61.36 g, IPDI 66.26 g
Step 2: PE2 100.29 g, product obtained in step 1:149.71 g.

Synthesis Example 11

Polymer P11 (Hyperbranched Polyester Based on Poly-THF and Citric Acid Mono Hydrate Modified with IPDI, and MPEG1/FAPAG5 in a Weight Ratio of 1:4.01)
11.1 Synthesis of Hyperbranched Polyester PE2
The synthesis of PE2 was carried out as in synthesis example 3.1
11.2 Modification of the Hyperbranched Polyester PE2 with IPDI, and MPEG1/FAPAG5 in a Weight Ratio of 1:4.01

Step 1: MPEG1 22.00 g, FAPAG5 88.28 g, IPDI 19.73 g
Step 2: PE2 47.28 g, product obtained in step 1:102.72 g.

Synthesis Example 12

Polymer P12 (Hyperbranched Polyester Based on Poly-THF and Citric Acid Mono Hydrate Modified with IPDI, and MPEG1/FAPAG5 in a Weight Ratio of 3.5:1)
12.1 Synthesis of Hyperbranched Polyester PE2
The synthesis of PE2 was carried out as in synthesis example 3.1
12.2 Modification of the Hyperbranched Polyester PE2 with IPDI, and MPEG1/FAPAG5 in a Weight Ratio of 3.5:1
Step 1: MPEG1 89.81 g, FAPAG5 25.66 g, IPDI 34.53 g
Step 2: PE2 79.12 g, product obtained in step 1:120.88 g.

Synthesis Example 13

Polymer P13 (Hyperbranched Polyester Based on Poly-THF and Citric Acid Mono Hydrate Modified with IPDI, and MPEG1/FAPAG1 in a Weight Ratio of 1.53:1)
13.1 Synthesis of Hyperbranched Polyester PE2
The synthesis of PE2 was carried out as in synthesis example 3.1
13.2 Modification of the Hyperbranched Polyester PE2 with IPDI, and MPEG1/FAPAG1 in a Weight Ratio of 1.53:1
Step 1: MPEG1 58.86 g, FAPAG1 38.51 g, IPDI 22.63 g
Step 2: PE2 84.52 g, product obtained in step 1:95.48 g.

Synthesis Example 14

Polymer P14 (Hyperbranched Polyester Based on Poly-THF and Citric Acid Mono Hydrate Modified with IPDI, and MPEG2/FAPAG2 in a Weight Ratio of 2.58:1)
14.1 Synthesis of Hyperbranched Polyester PE2
The synthesis of PE2 was carried out as in synthesis example 3.1
14.2 Modification of the Hyperbranched Polyester PE2 with IPDI, and MPEG2/FAPAG2 in a Weight Ratio of 2.58:1
Step 1: MPEG2 178.98 g, FAPAG2 69.42 g, IPDI 51.60 g
Step 2: PE2 58.34 g, product obtained in step 1:141.66 g.

Synthesis Example 15

Polymer P15 (Hyperbranched Polyester Based on Poly-THF and Citric Acid Mono Hydrate Modified with IPDI, and MPEG2/FAPAG1 in a Weight Ratio of 2.04:1)
15.1 Synthesis of Hyperbranched Polyester PE2
The synthesis of PE2 was carried out as in synthesis example 3.1
15.2 Modification of the Hyperbranched Polyester PE2 with IPDI, and MPEG2/FAPAG1 in a Weight Ratio of 2.04:1
Step 1: MPEG2 196.74 g, FAPAG1 96.54 g, IPDI 56.72 g
Step 2: PE2 55.91 g, product obtained in step 1:144.09 g.

Synthesis Example 16

Polymer P16 (Hyperbranched Polycarbonate Based on on DEC and TMP-PO2 Modified with IPDI, and MPEG1/FAPAG1/FAPAG2 in a Weight Ratio of 1.66:1.27:1)
16.1 Synthesis of Hyperbranched Polycarbonate PC2
The synthesis of PC2 was carried out as in synthesis example 4.1
16.2 Modification of the Hyperbranched Polycarbonate PC2 with IPDI, and MPEG1/FAPAG1/FAPAG2 in a Weight Ratio of 1.66:1.27:1
Step 1: MPEG1 120.49 g, FAPAG1 91.97 g, FAPAG2 72.69 g, IPDI 64.84 g
Step 2: PC2 61.46 g, product obtained in step 1:138.54 g.

Synthesis Example 17

Polymer P17 (Hyperbranched Polycarbonate Based on on DEC and TMP-PO2 Modified with IPDI, and MPEG2/FAPAG1/FAPAG2 in a Weight Ratio of 1.75:1:1.58)
17.1 Synthesis of Hyperbranched Polycarbonate PC2
The synthesis of PC2 was carried out as in synthesis example 4.1
17.2 Modification of the Hyperbranched Polycarbonate PC2 with IPDI, and MPEG2/FAPAG1/FAPAG2 in a Weight Ratio of 1.75:1:1.58
Step 1: MPEG2 100.60 g, FAPAG1 57.59 g, FAPAG2 91.04 g, IPDI 550.76 g
Step 2: PC2 57.66 g, product obtained in step 1:142.34 g.

Synthesis Example 18

Polymer P18 (Hyperbranched Polyester Based on Poly-THF and Citric Acid Mono Hydrate Modified with IPDI, and MPEG2/FAPAG1/FAPAG2 in a Weight Ratio of 1.75:1:1.58)
18.1 Synthesis of Hyperbranched Polyester PE2
The synthesis of PE2 was carried out as in synthesis example 3.1
18.2 Modification of the Hyperbranched Polyester PE2 with IPDI, and MPEG2/FAPAG1/FAPAG2 in a Weight Ratio of 1.75:1:1.58
Step 1: MPEG2 100.60 g, FAPAG1 57.59 g, FAPAG2 91.04 g, IPDI 50.76 g
Step 2: PE2 67.23 g, product obtained in step 1:132.77 g.

Synthesis Example 19

Polymer P19 (Hyperbranched Polyamide Based on TMBTC, AEE and MDA Modified with IPDI and MPEG1/FAPAG7 in a Weight Ratio of 2.73:1)
19.1 Synthesis of Hyperbranched Polyamide PA1
Trimethyl-1,2,4-tricarboxylate (TMBTC, 190 g), 2-(2-aminoethoxy) ethanol (AEE, 99 g) and sodium methoxide (0.8 g) were added to the reaction vessel and heated to 100° C. under a nitrogen atmosphere. After the initial reaction finished to completion (analysis via HC-titration) 4,4-diaminophenyl methane (MDA, 112 g) was added. The reaction was then heated to 120° C. and monitored via HCl titration until completion.
19.2 Modification of the Hyperbranched Polyamide PA1 with IPDI and MPEG 1/FAPAG7 in a Weight Ratio of 2.73:1
Step 1: MPEG1 183 g, FAPAG7 67 g, IPDI 70 g
Step 2: PA1 55 g, product obtained in step 1:145 g.

Synthesis Example 20

Polymer 20 (Hyperbranched Polyamide Based on Citric Acid and AEE, Modified with IPDI and MPEG1/FAPAG7 in a Weight Ratio of 2.73:1)
20.1 Synthesis of Hyperbranched Polyamide PA2
Citric acid triethyl ester (199 g), 2-(2-aminoethoxy) ethanol (AEE, 95 g) and sodium methoxide (0.8 g) were added to the reaction vessel and heated to 100° C. under a nitrogen atmosphere. After the initial reaction finished to completion (analysis via HC-titration) 4,4-diaminophenyl methane (MDA, 107 g) was added. The reaction was then heated to 120° C. and monitored via HCl titration until completion.
20.2 Modification of the Hyperbranched Polyamide PA 2 with IPDI and MPEG1/FAPAG7 in a Weight Ratio of 1:2.73
  Step 1: MPEG1 183 g, FAPAG7 67 g, IPDI 70 g
  Step 2: PA2 57 g, product obtained in step 1:143 g.

Synthesis Example 21

Polymer 21 (Hyperbranched Polyurea Based on HI100, n-Butanol and Polyether Amine D230 Modified with IPDI and MPEG/FAPAG6 in a Weight Ratio 1:3.5)
21.1 Synthesis of Hyperbranched Polyurea PU1
Basonat HI100 (120 g) was added to the reaction vessel and heated to 80° C. under a nitrogen atmosphere. Then n-butanol (92 g) was added and stirred for 4-5 h, the reaction was cooled to room temperature and polyether amine D230 (89 g) was added slowly and gradually heated to 170° C. and dibutyl tin dilaurate was added (69 mg). The progress of the reaction was monitored via HCl titration and stopped at ca. 50% conversion.
21.2 Modification of PU1 with IPDI and MPEG1/FAPAG6 in a weight ratio of 1:3.5
  Step 1: MPEG1 192 g, FAPAG6 55 g, IPDI 74 g,
  Step 2: PU1 72 g, product obtained in step 1:72 g.

Synthesis Example 22

Polymer P22 (Hyperbranched Polyurea Based on Basonat HI 100, n-Butanol and Polyether Amine D230, Modified with MPEG1/FAPAG4 in a Weight Ratio of 1:2.55)
22.1 Synthesis of Hyperbranched Polyurea PU2
Basonat HI100 (318 g) was added to the reaction vessel and heated to 80° C. under a nitrogen atmosphere. Then n-butanol (245 g) was added and stirred for 4-5 h, the reaction was cooled to room temperature and polyether amine D230 (236 g) was added slowly and gradually heated to 170° C. and dibutyl tin dilaurate was added (184 mg). The progress of the reaction was monitored via HCl titration and stopped at ca. 50% conversion.
22.2 Modification of PU2 with IPDI and MPEG1/FAPAG4 in a Weight Ratio of 1:2.55
  Step 1 MPEG1 186 g, FAPAG4 73 g, IPDI 71 g,
  Step 2 PU2 47 g, product obtained in step 1 76 g, reaction in isobutanol (76 g).

Synthesis Example 23

Polymer P23 (Hyperbranched Polyurethane PUR1, Based on Lupranol VP 9319 and MDI, Modified with MPEG1 and FAPAG4 in a Weight Ratio of 1:2.53)
23.1 Synthesis of Hyperbranched Polyurethane PUR1
Lupranol VP 9319 (153 g) was added to the reaction vessel under nitrogen, then MDI (74 g) was dissolved in acetone (74 g) and added in drops. The starting NCO-Value was determined and the catalyst was added. After the reaction had run to 50% completion, diethanol amine (31 g) was added.
23.2 Modification of PUR1 with IPDI and MPEG1/FAPAG4 in a Weight Ratio of 1:2.53
  Step 1: MPEG1 129 g, FAPAG4 51 g, IPDI 50 g
  Step 2 PUR1 22 g, product obtained from step 1 105 g, in acetone (73 g), target NCO value: O.

Synthesis Example 24

Polymer P24 (Hyperbranched Polyurethane PUR2 Based on Basonat HI100 and Poly-THF, Modified with MPEG1 and FAPAG4 in a Weight Ratio of MPEG1/FAPAG7 1:2.73)

24.1 Synthesis of Hyperbranched Polyurethanes PUR2
Basonat HI 100 was added to the reaction vessel and heated to 60° C. under nitrogen atmosphere. Then poly-THF was added and the NCO-value was determined. The reaction mixture was stirred until the target NCO was reached (ca. 50% conversion) and diethanolamine was added to stop the reaction. The reaction mixture was then stirred at 100° C. afterwards to give the final product.
24.2 Modification of PUR2 with IPDI and MPEG1/FAPAG7 in a Weight Ratio of 1:273
  Step 1: MPEG1 314 g, FAPAG7 115 g, IPDI 121 g,
  Step 2 PUR2 23 g, product obtained from step 1 177 g.

Application Example 1

Increased uptake and retention of pesticide in leaves:
An aqueous suspension concentrate ("SC1") was prepared containing 300 g/l fluxapyroxad, 1,2-propylene glycol, anionic phenolsulfonic acid-urea-formaldehyde condensate surfactant, sodium salt of naphthalene sulfonate condensate, antibacterial agent, antifoaming agent, and hyperbranched polymer of the invention. The spray mixture was applied at a rate of 200 l/ha, 12.5 g/ha pesticide and 250 g/ha polymer of the invention.

The uptake of the pesticide in the leave was determined as decribed by Berghaus R, Nolte M, Reinold A 2010. "Optimization of agrochemical formulations by adjuvants using lab track sprayer and H PLC-MS-MS analysis". In: Baur P and Bonnet M ed. Proc. 9th Intern. Symp. on Adjuvants for Agrochemicals. ISAA 2010 Freising, Germany. Pp. 239-244: Wheat plants (Triticumaestivum variety Melon) were used. Subsequently to spraying, the plants were cultivated again in the greenhouse under ambient conditions. After 8 days samples of 10-15 treated leaves were cut off and weighed. Leaves were cut into small pieces, and washed with 50% methanol in demineralized water as washing medium for 5 min. Then, the washing medium was separated from the leaves. The leaves were washed again with washing medium for 5 min. Both washing media were combined and diluted for analysis.

Finally, the leaves were transferred to a vial containing the extraction medium (75% methanol, 20% water and 5% HCl) and homogenized using a Polytron PT 6100 dispersing unit (Kinematica, CH) for 2 min. 10 ml of the extract were centrifuged with 4000 rpm for 5 min. 2 ml of the supernatant were treated with 2 ml NaOH (0.2 mol/L) and 5 ml cyclohexane, and stirred for 30 min and centrifuged subsequently. 1 ml of the cyclohexane phase was transferred to a glass vial and dried (Liebisch $N_2$ Evaporator, Germany). The residue was solubilized in methanol/water 50:50 and analyzed by HPLC-MS/MS. In addition, unsprayed plants were treated in the same way to see whether they are contaminated. Unsprayed leaves were spiked with standard active ingredient to determine the recovery of active ingredient during washing and extracting steps. According to the recovery rate the measured sample values were corrected. Retention (total amount of active found in and on the plant) is equal to the sum of active concentrations found during washing and extracting steps.

The results that are given in Table 1 show that the usage of invented adjuvants drastically increases the uptake of pesticide. The comparative branched polymers GM 903/0 and ABC showed that this modification resulted in an increased uptake and retention of the active.

TABLE 1

| added polymer | Uptake (mg/kg leave) | Retention (mg/kg leaf) |
|---|---|---|
| none | 0.4 | 2.4 |
| P8 | 1.26 | 4.7 |
| P10 | 0.9 | 5.7 |
| P10 | 1.49 | 6.5 |
| P3 | 0.90 | 4.5 |
| P6 | 0.67 | 3.7 |
| P12 | 1.1 | 6.4 |
| P13 | 1.3 | 6.1 |
| P14 | 1.2 | 7.5 |
| P15 | 1.8 | 7.4 |
| P7 | 1.4 | 6.3 |
| P16 | 2.6 | 7.4 |
| P5 | 2.1 | 5.2 |
| P17 | 2.0 | 7.3 |
| P18 | 1.5 | 5.3 |

Application Example 2A

An aqueous suspension concentrate ("SC1") was prepared as in Application Example 1. The pesticidal activity was tested in greenhouse tests on wheat variety Monopol, which was infected with the fungi *Puccinia* Recondata/*Tritici*. The plants were treated with SC1 three days after the inoculation at a use rate of 25 and 8.3 pesticide per ha (200 l water/ha). The use rate of the polymers of the invention was kept constant at 250 g per ha. The percentage of the infected leaf surface ares (7 days after inoculation) is summarized in Table 2.

The data shows that the composition with the polymers according to the invention has a higher pesticidal activity compared to the control without polymer.

TABLE 2

| | added polymer | % Use rate of active | |
|---|---|---|---|
| | | 100% | 33% |
| | | % infected leaf area | |
| AE2-A.1 | untreated | 80% | |
| AE2-A.2 | no polmyer | 79% | 80% |
| AE2-A.3 | P1 | 2% | 18% |
| AE2-A.4 | P8 | 12% | 75% |
| AE2-A.5 | P9 | 30% | 66% |
| AE2-A.6 | P10 | 10% | 76% |
| AE2-A.7 | P3 | 5% | 33% |
| AE2-A.8 | P6 | 6% | 46% |
| AE2-A.9 | P13 | 5% | 18% |
| AE2-A.10 | P11 | 14% | 58% |
| AE2-A.11 | P14 | 2% | 15% |
| AE2-A.12 | P7 | 10% | 30% |
| AE2-A.13 | P16 | 8% | 25% |
| AE2-A.14 | P5 | 4% | 26% |
| AE2-A.15 | P17 | 5% | 35% |
| AE2-A.16 | P18 | 4% | 25% |

Application Example 2B

The above greenhouse tests were also made with a suspension concenctrate "SC2" of the triazole fungicide 2-[4-(4-chlorophenoxy)-2-(trifluoromethyl)phenyl]-1-(1H-1,2,4-triazol-1-yl)propan-2-ol ("triazole fungicide") (100 g/ha) instead of fluxapyroxad. The results are summarized in Table 3.

TABLE 3

| | added polymer | % Use rate of active | |
|---|---|---|---|
| | | 100% | 33% |
| | | % infected leaf area | |
| AE 2-B.1 | Untreated | 89% | |
| AE 2-B.2 | no polmyer | 83% | 91% |
| AE 2-B.3 | P3 | 8% | 11% |

Application Example 3

Solubilization measurements were carried out with a highthroughput screening robot. In this set up 10 mg solid active and 500 μm of the respective 3 wt % liquid polymer solution (in CIPAC water D) were dosed into wells on a micro titer plate. After the addition of stirring bars and 24 hours incubation time the samples were filtrated through polypropylene filters in order to separate dissolved active and its solid form. The amount of solubilized active was determined by UV/VIS spectroscopy. The solubilities of various actives are summarized in Tables 4 to 8.

TABLE 4

| Increased solubility of fluxapyroxad | |
|---|---|
| added polymer | Solubility in pmm |
| none | 10 |
| P1 | 749 |
| P10 | 839 |
| P3 | 1051 |
| P11 | 1429 |
| P16 | 1221 |
| P5 | 1052 |
| P17 | 1308 |
| P18 | 1216 |

TABLE 5

| Increased solubility of fipronil | |
|---|---|
| added polymer | Solubility in pmm |
| none | 12 |
| P1 | 1715 |
| P3 | 1723 |

TABLE 6

| Increased solubility of the triazole fungicide 2-[4-(4-chlorophenoxy)-2-(trifluoromethyl)phenyl]-1-(1H-1,2,4-triazol-1-yl)propan-2-ol | |
|---|---|
| added polymer | Solubility in pmm |
| none | 15 |
| P11 | 2274 |

TABLE 7

| Increased solubility of fenofibrate | |
|---|---|
| added polymer | Solubility in pmm |
| none | 0 |
| P6 | 2282 |

TABLE 8

Increased solubility of carbamazepine

| added polymer | Solubility in pmm |
|---|---|
| none | 181 |
| P1 | 848 |
| P3 | 826 |
| P6 | 1201 |

Application Example 4

An aqueous suspension concentrate "SC4" was prepared comprising 80 g/l fluxapyroxad, 80 g/l hyperbranched polymer (see Table 9), 25 g/l 1,2-propylene glycol, 13 g/L sodium salt of naphthalene sulfonate condensate, 1.5 g/l xanthan gum, 5 g/l anionic phenolsulfonic acid-urea-formaldehyde condensate, silicon defoamer, and antibacterials. For comparison, the aqueous suspension concentrate "SC4" was prepared without the addition of any hyperbranched polymer ("No Polymer"). The suspension concentrates were stored for 14 days at 20° C. or at 40° C. The stability of the formulation was determined by using instrument Malvern. D90 is the value in μm that 90% (volume/volume) of the particles existing in the formulation have a size smaller this value. An increase in D 90 is an indication for the destabilization of SC formulations.

For comparison, FAPAG5 and FAPAG8 were used. These comparative polymers resulted in an clear increase of particle size during storage.

TABLE 9

Particle size D90 [μm] during storage of suspension concentrate "SC4"

| added polymer | D (90) | | | |
|---|---|---|---|---|
| | 0 d | 14 d at 20° C. | 14 d at 40° C. | 14 d at 50° C. |
| No Polymer | 2.0 | 2.0 | 2.0 | 2.0 |
| P1 | 1.9 | 2.0 | 2.0 | 2.0 |
| P3 | 2.0 | 1.8 | 1.9 | 2.0 |
| P5 | 2.0 | 2.0 | 2.1 | 2.0 |
| P6 | 2.0 | 1.9 | 1.9 | 2.2 |
| P7 | 2.2 | 1.9 | 2.0 | 2.1 |
| P8 | 2.0 | 1.9 | 1.9 | 2.0 |
| P9 | 2.0 | 2.0 | 2.0 | 2.1 |
| P10 | 2.1 | 2.0 | 2.0 | 2.1 |
| P11 | 1.8 | 2.0 | 2.0 | 2.0 |
| P12 | 2.0 | 2.0 | 2.0 | 2.4 |
| P13 | 2.0 | 1.9 | 1.9 | 2.0 |
| P14 | 2.0 | 2.0 | 2.1 | 2.2 |
| P15 | 2.2 | 2.0 | 2.0 | 2.2 |
| P16 | 2.0 | 2.0 | 2.1 | 3.2 |
| P17 | 2.0 | 2.0 | 2.0 | 2.1 |
| P18 | 2.1 | 2.0 | 2.1 | 2.0 |
| FAPAG5 | 2.0 | 6.5 | 8.2 | — |
| FAPAG8 | 2.0 | 7.9 | 7.8 | — |

Application Example 5

Table 10 provides an overview of the composition and water solubility (20 wt %) at room temperature of some hyperbranched polymers of the invention. The components in the table do not add up to 100 wt % because the amount of linker b) is not included.

TABLE 10

Percentages of components of polymer and solubilities

| Polymer | Polycondensate % w/w | MPEG's % w/w | FAPAGs % w/w | Water solubility |
|---|---|---|---|---|
| P1 | 9 | 45 | 29 | Soluble |
| P3 | 64 | 18 | 12 | Soluble |
| P5 | 28 | 29 | 17 | Soluble |
| P6 | 35 | 32 | 12 | Soluble |
| P7 | 10 | 47 | 25 | Soluble |
| P8 | 35 | 30 | 23 | Soluble |
| P9 | 39 | 34 | 14 | Soluble |
| P10 | 40 | 34 | 12 | Soluble |
| P11 | 32 | 12 | 46 | Soluble |
| P12 | 40 | 63 | 10 | Soluble |
| P13 | 47 | 26 | 17 | Soluble |
| P14 | 35 | 28 | 28 | Soluble |
| P15 | 28 | 40 | 20 | Soluble |
| P16 | 31 | 24 | 18 | Soluble |
| P17 | 29 | 24 | 14 | Soluble |
| P18 | 34 | 22 | 13 | Soluble |

For comparison, the solubilities of building blocks or hyperbranched polymers with only FAPAG but no MPEG were tested and summarized in Table 11.

The building blocks FAPAG1, FAPAG5 and FAPAG8 were not soluble ("n.s.") at 10 wt % in water at room temperature. For comparison, the hyperbranched polymers P1, P3, P5, P6, and P15-18 (containing FAPAG1), P11 and P12 (containing FAPAG5) and P10 (containing FAPAG8) were soluble at 20 wt % in water (cf Table 10).

The polymers CP1, CP2, CP3 and CP4 contained only FAPAG but no MPEG were not soluble in water ("n.s.") neither at 20 wt %, nor at 1 wt %. Comparable polymers according to the invention which contained a mixture of FAPAG and MPEG were soluble in water.

TABLE 11

Percentages of components of comparative polymer and solubilities

| Polymer | Polycondensate % w/w | MPEG's % w/w | FAPAGs % w/w | Water solubility |
|---|---|---|---|---|
| FAPAG1 | — | — | — | n.s. |
| FAPAG5 | — | — | — | n.s. |
| FAPAG8 | — | — | — | n.s. |
| CP1 | 7 | 0 | 79 | n.s. |
| CP2 | 31 | 0 | 59 | n.s. |
| CP3 | 61 | 0 | 30 | n.s. |
| CP4 | 28 | 0 | 62 | n.s. |

The synthetic details of polymers CP1 to CP4 were as follows: The polymer CP1 was prepared according to polmyer P1, and had the same core (polycarbonate PC1) like the polymer P1 and P7, but the weight ratio of MPEG:FAPAG was 0:100. The polymer CP2 was prepared according to polymer P3, and had the same core (polyester PE1) like the polymer P3 and P10, but the weight ratio of MPEG:FAPAG was 0:100. The polymer CP3 was prepared according to polymer P11, and had the same core (polyester PE2) like the polymer P11, but the weight ratio of MPEG:FAPAG was 0:100. The polymer CP4 was prepared according to polymer P10, and had the same core (polyester PE2) like the polymer P10, but the weight ratio of MPEG:FAPAG was 0:100.

The invention claimed is:

1. Hyperbranched polymer comprising
   a) a hyperbranched polycondensate with hydroxyl end groups, amino end groups, or a combination thereof condensed to b) one or more linkers connected to
c1) one or more polyethylene glycol monomethyl ethers and
c2) one or more poly($C_2$-$C_3$)alkylene glycol mono-($C_8$-$C_{22}$)-alkyl ethers, wherein the weight ratio of components c1):c2) is from 9:1 to 1:9.

2. The hyperbranched polymer according to claim 1, wherein the hyperbranched polycondensate (a) is a polycarbonate (a1), a polyester (a2), a polyimide (a3), a polyurethane (a4) or a polyurea (a5).

3. The hyperbranched polymer according to claim 1, wherein the polycondensate (a) amounts to 5 to 70 wt.-% of the total weight of the hyperbranched polymer.

4. The hyperbranched polymer according to claim 1, wherein the linkers (b) are polyisocyanates with a functionality of 1.5 to 4.5 isocyanate groups per molecule.

5. The hyperbranched polymer according to claim 1, wherein the amount of components (c1) and (c2) based on the total amount of the hyperbranched polymer is from 90 to 30 wt.-%.

6. The hyperbranched polymer according to claim 1, wherein the polyethylene glycol monomethyl ether (c1) has a molecular weight of 300 to 2000 g/mol.

7. The hyperbranched polymer according to claim 1, wherein the polyalkylene glycol monoalkyl ethers (c2) are compounds of the formula

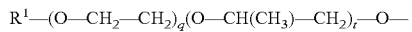

wherein
each $R^1$ is independently linear or branched $C_8$-$C_{22}$-alkyl;
q is a natural number from 1 to 50; and
r is 0 or is a natural number from 1 to 30, with the proviso that $5 \leq q+r \leq 50$.

8. The hyperbranched polymer according to claim 1, wherein the hyperbranched polycondensate (a) is a hyperbranched polycarbonate (a1) which comprises an alcohol (B1) in polymerized form, wherein the alcohol (B1) is a trifunctional or higher-functionality polyetherol based on alcohols which have at least three OH groups, and $C_2$-$C_{24}$ alkylene oxide.

9. The hyperbranched polymer of claim 1, wherein the weight ratio of components (c1) to (c2) is from 7:3 to 1:9.

10. The hyperbranched polymer of claim 1, wherein the weight ratio of components (c1) to (c2) is from 7:3 to 2:8.

11. The hyperbranched polymer of claim 1, wherein the weight ratio of components (c1) to (c2) are from 5:1 to 1:3.

12. A process for producing hyperbranched polymer according to claim 1 comprising the steps of:

α-1 reacting a hyperbranched polycondensate with hydroxyl end groups, amino end groups, or a combination thereof with a linker (b), and α-2 reacting the product of step α-1 with a mixture of at least one polyethylene glycol monomethyl ether (c1) and at least one poly($C_2$-$C_3$)-alkylene glycol mono-($C_8$-$C_{22}$)-alkyl ether, wherein the weight ratio of c1):c2) is from 9:1 to 1:9.

13. A composition comprising the hyperbranched polymer according to claim 1 and an active ingredient.

14. The composition according to claim 13, wherein the composition is an agrochemical composition comprising a pesticidal active ingredient.

15. A process for producing the composition according to claim 1 further comprising an active ingredient, the process comprising the step of contacting a hyperbranched polymer of claim 1 and the active ingredient.

16. A method for controlling phytopathogenic fungi or undesired vegetation or insect or acarid infestations or for regulating the growth of plants, comprising at least one of:
applying a pesticidal composition according to claim 14 to the pests;
applying a pesticidal composition according to claim 14 to undesired plants;
applying a pesticidal composition according to claim 14 to plants to be protected;
applying a pesticidal composition according to claim 14 the soil of the plants to be protected;
applying a pesticidal composition according to claim 14 to where the undesired plants grow;
and combinations thereof.

17. A process for producing hyperbranched polymer according to claim 1 comprising the steps:

β-1 reacting a mixture of at least one polyethylene glycol monomethyl ether (c1) and at least one poly($C_2$-$C_3$)-alkylene glycol mono-($C_8$-$C_{22}$)-alkyl ether, wherein the weight ratio of c1):c2) is from 9:1 to 1:9 with a linker (b), and β-2 reacting the product of step β-1 with a hyperbranched polymer with a plurality of end groups selected from hydroxyl end groups, amino end groups, and combinations thereof.

18. A process for producing the composition according to claim 1 wherein the composition of claim 1 is an agrochemical composition further comprising a pesticidal active ingredient, the process comprising the step of contacting a hyperbranched polymer of claim 1 and the pesticidal active ingredient.

* * * * *